(12) United States Patent
Shohat et al.

(10) Patent No.: US 9,549,719 B2
(45) Date of Patent: *Jan. 24, 2017

(54) RAPID LAPAROSCOPY EXCHANGE SYSTEM AND METHOD OF USE THEREOF

(71) Applicant: EON Surgical Ltd., Tel-Aviv (IL)

(72) Inventors: Shaul Shohat, Kfar HaOranim (IL); Danny Farin, Hod-Hasharon (IL); Yehoda Bachar, Givat-Shmuel (IL); Ronny Winshtein, Tel-Aviv (IL)

(73) Assignee: EON SURGICAL LTD., Tel-Aviv (IL)

( * ) Notice: Subject to any disclaimer, the term of this patent is extended or adjusted under 35 U.S.C. 154(b) by 53 days.

This patent is subject to a terminal disclaimer.

(21) Appl. No.: 14/274,281

(22) Filed: May 9, 2014

(65) Prior Publication Data

US 2014/0343360 A1     Nov. 20, 2014

Related U.S. Application Data

(63) Continuation of application No. 13/010,661, filed on Jan. 20, 2011, now Pat. No. 8,721,539.
(Continued)

(51) Int. Cl.
*A61B 1/32*     (2006.01)
*A61B 17/02*    (2006.01)
(Continued)

(52) U.S. Cl.
CPC ....... *A61B 17/0218* (2013.01); *A61B 1/00154* (2013.01); *A61B 17/3403* (2013.01);
(Continued)

(58) Field of Classification Search
CPC . A61B 17/02; A61B 17/1714; A61B 17/0218; A61B 17/3403; A61B 2017/00362
(Continued)

(56) References Cited

U.S. PATENT DOCUMENTS 5,300,035 A     4/1994   Clement
5,375,588 A    12/1994   Yoon
(Continued)

FOREIGN PATENT DOCUMENTS

JP      2007-534380 A    11/2007
WO         94/22382 A1   10/1994
(Continued)

*Primary Examiner* — Mary Hoffman
*Assistant Examiner* — Tara R Carter
(74) *Attorney, Agent, or Firm* — Baker and Hostetler LLP

(57) ABSTRACT

A system for positioning an interchangeable tool in a body cavity includes a channel having a lumen in direct communication with the body cavity, a tool introducer having a longitudinal axis and a distal end, and a tool holder covering at least a portion of the interchangeable tool that is pivotally connected to the tool introducer allowing angular positioning of the interchangeable tool after the tool holder emerges from the channel into the body cavity. A method for engaging an interchangeable tool with a distal portion of a tool manipulator in a body cavity includes inserting a tool introducer into a channel, orienting the distal portion of the tool manipulator in the body cavity, emerging the interchangeable tool from the channel into the body cavity, and positioning the interchangeable tool eccentrically to the lumen of the channel.

19 Claims, 14 Drawing Sheets

Related U.S. Application Data

(60) Provisional application No. 61/296,485, filed on Jan. 20, 2010.

(51) Int. Cl.
*A61B 17/34* (2006.01)
*A61B 1/00* (2006.01)
A61B 17/00 (2006.01)
A61B 17/29 (2006.01)

(52) U.S. Cl.
CPC .............. *A61B 2017/00362* (2013.01); *A61B 2017/2931* (2013.01); *A61B 2017/3407* (2013.01); *A61B 2017/3466* (2013.01)

(58) Field of Classification Search
USPC .............. 606/96–98, 205–208; 600/201–230
See application file for complete search history.

(56) References Cited

U.S. PATENT DOCUMENTS

| | | |
|---|---|---|
| 5,441,059 A | 8/1995 | Dannan |
| 5,645,549 A * | 7/1997 | Boyd ................ A61B 18/1402 606/45 |
| 5,658,306 A | 8/1997 | Kieturakis et al. |
| 6,146,402 A | 11/2000 | Munoz |
| 6,197,002 B1 | 3/2001 | Peterson |
| 6,312,443 B1 | 11/2001 | Stone |
| 8,137,267 B2 | 3/2012 | Shelton, IV et al. |
| 8,852,253 B2 | 10/2014 | Mafi |
| 2003/0130693 A1 | 7/2003 | Levin et al. |
| 2005/0234294 A1 | 10/2005 | Saadat et al. |
| 2006/0200184 A1 | 9/2006 | Deal |
| 2007/0073323 A1 | 3/2007 | Carter et al. |
| 2007/0179507 A1 | 8/2007 | Shah |
| 2008/0228213 A1 | 9/2008 | Blakeney et al. |
| 2008/0287926 A1 | 11/2008 | Abou El Kheir |
| 2009/0259175 A1 | 10/2009 | Nordgren |
| 2009/0259184 A1 | 10/2009 | Okoniewski |
| 2009/0270676 A1 | 10/2009 | Sicvol |

FOREIGN PATENT DOCUMENTS

| | | |
|---|---|---|
| WO | 03-015848 A9 | 2/2003 |
| WO | 2005-122921 A2 | 12/2005 |
| WO | 2007008332 A3 | 1/2007 |
| WO | 2007073931 A1 | 7/2007 |

* cited by examiner

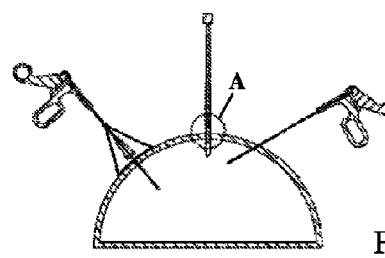
FIG. 5A
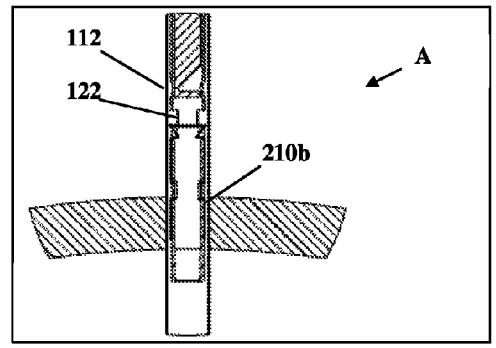
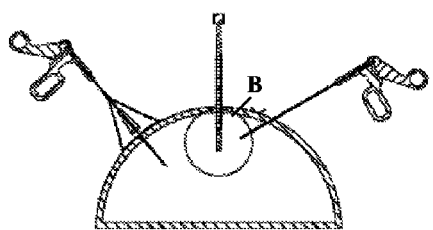
FIG. 5B
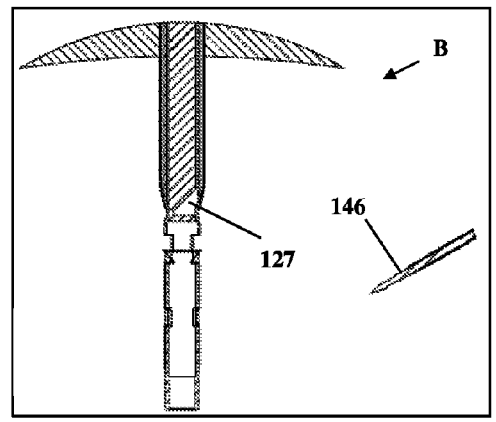
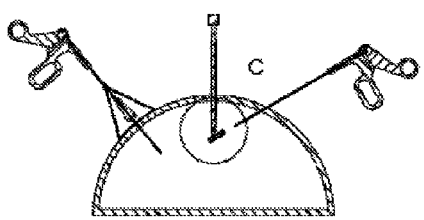
FIG. 5C
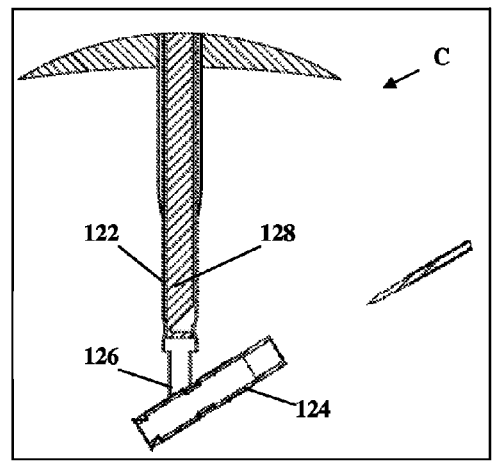

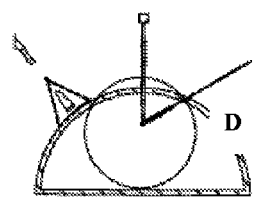
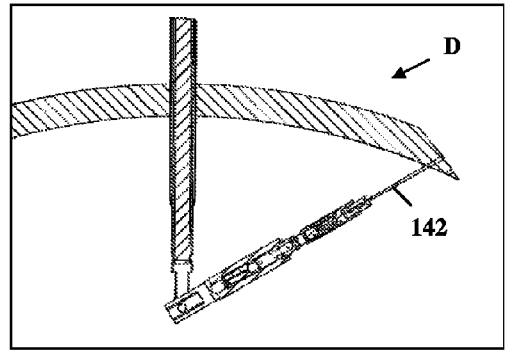
FIG. 5D
FIG. 5E
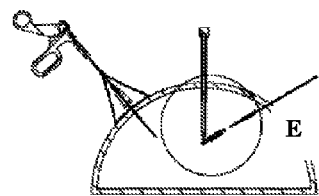
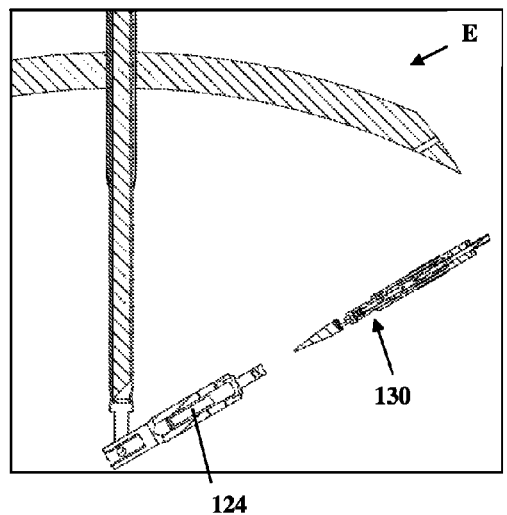
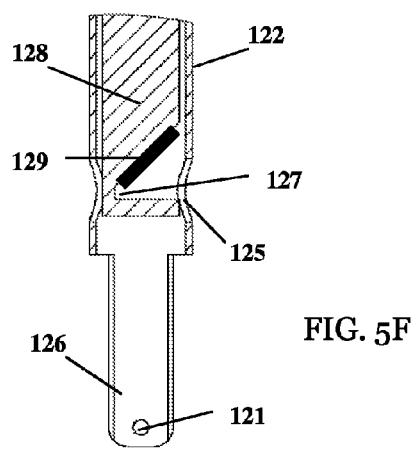
FIG. 5F

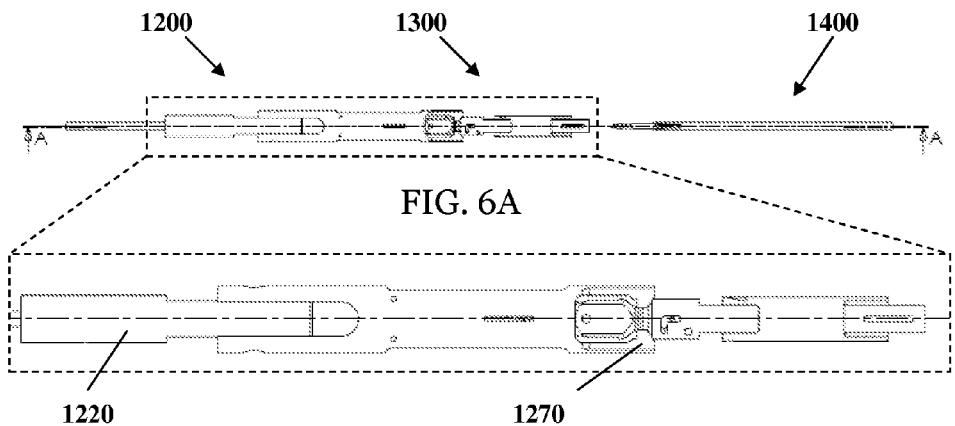
FIG. 6A
FIG. 6B
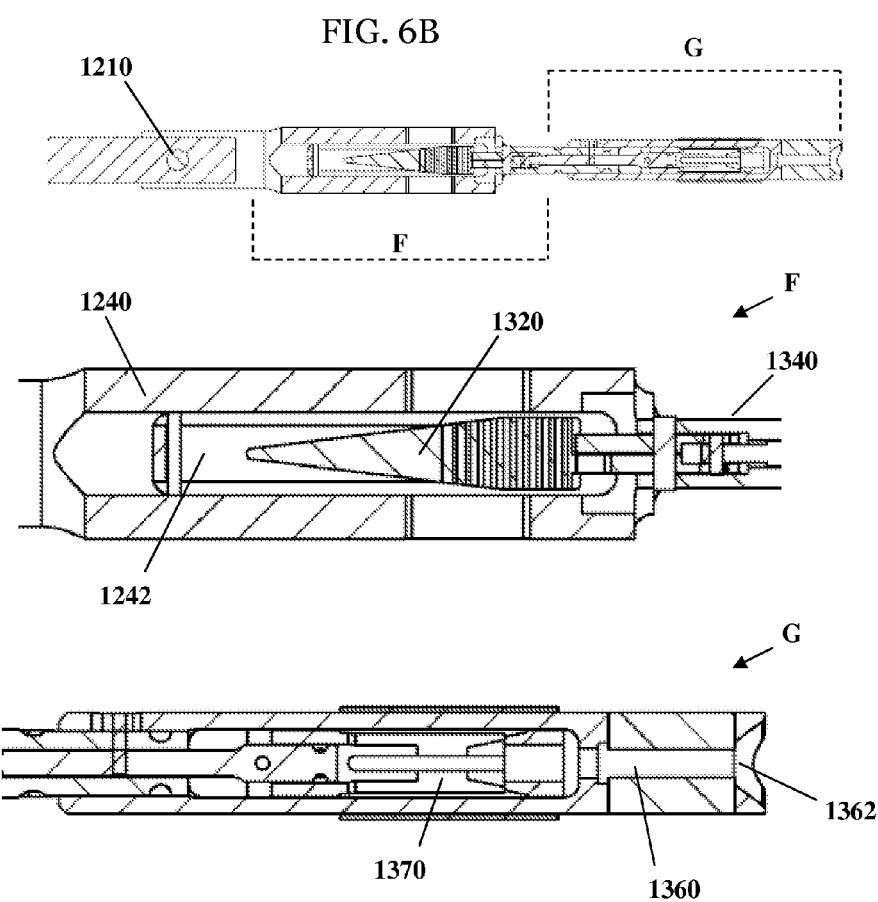

RAPID LAPAROSCOPY EXCHANGE SYSTEM AND METHOD OF USE THEREOF

RELATED APPLICATIONS

This application is a continuation of U.S. Non-Provisional application Ser. No. 13/010,661, filed on Jan. 20, 2011, which claims priority to U.S. Provisional Application Ser. No. 61/296,485, filed Jan. 20, 2010, both entitled Rapid Laparoscopy Exchange System And Method Of Use Thereof, and both of which are hereby incorporated by reference herein in their entireties.

FIELD OF THE INVENTION

The present invention generally relates to surgical methods and devices, and more specifically to laparoscopic and/or any endoscopic related surgical interventions.

BACKGROUND OF THE INVENTION

Laparoscopic or minimally invasive surgery includes the use of several relatively small ports into the abdomen by which different types of instrumentation and accessories are introduced and used for different surgical interventions (usually performed under endoscopic vision). Although usually considered superior in several aspects to open surgery, the use of plurality of 5 to 15 mm ports still leads to local pain, scars, and possibly port related complications such as hernia in scars and the need for one or two assistants in addition to the surgeon. Laparoscopic methods and surgical device are described, for example, in U.S. Pat. Nos. 5,980,493, 7,593,777 and 7,316,699, the disclosures of which are fully incorporated herein by reference.

In past years, new versions of laparoscopic systems and approaches were introduced to overcome several of the "classic" laparoscopy disadvantages, mainly the Single-Port Access (SPA) and the Needlescopy approaches. In SPA the surgeon operates almost exclusively through a single entry point, typically through the patient's navel, using access ports and hand instrument. Highly experienced and skilled physicians may still use standard laparoscopic hand instruments, although the use of a single port access decreases its triangulation and complicates maneuverability. The use of special-purpose articulating instrumentation was introduced to overcome this difficulty, although it is considered very expensive, necessitates special training and still involves complex surgical maneuverability.

Minilaparoscopy/needlescopic laparoscopy is intended to overcome the problems encountered in single port access surgery. While the advantages of SPA includes improved cosmetic, less abdominal wall pain and less incision related complications, this surgical approach has its disadvantages. The vision is partially obscured by the paralleled inserted instruments; there is minimal triangulation and limited maneuverability of the surgical instruments. Minilaparoscopy maintains the same mode of surgery as standard laparoscopy however there is only one trocar and all the rest of the instruments are connected to needle like shafts which are inserted with no trocar and therefore provide comparable cosmetic and painless results as SPA.

In needlescopy, the laparoscopic ports are replaced with small incisions, usually between 2 to 3 mm in diameter. The surgery is performed by inserting narrow guide tubes into the small incisions and then passing tiny instruments through the tubes, while using a small television camera for guidance. The small instruments have very slender tips which make dissection and tissue maneuvration very difficult. Furthermore the instrument tips may have a greater tendency to break and their removal may be cumbersome and difficult.

In order to avoid such difficulties while maintaining small incision porting, it has been advised to combine the single-port and the needlescopic approaches. This is achieved by first inserting regular-sized interchangeable end-effectors through a regular size single port access and then detachably attaching them to corresponding distal portions of needle-sized manipulators. The manipulators are protruding into abdomen cavity via miniature needlescopic type incisions. The concept and several device derivatives were described in the following patents, the disclosures of which are fully incorporated herein by reference.

U.S. Pat. No. 5,352,219 to Reddy describes a two-part modular tool and method for use thereof in conjunction with laparoscopic techniques enhances such techniques by enabling tools to be manipulated within a body cavity through small needle holes. The tool has an instrument head initially inserted through a laparoscopic port and an acuminate shaft which intracorporeally attaches to the instrument head. The instrument head is then manipulable through the needle hole at the site of desired use. The instrument head may be any tool configuration useful in surgical procedures which can be miniaturized to pass through a laparoscopic port.

U.S. Pat. No. 5,441,059 to Dannan describes a method of conducting minimally invasive surgery that includes the steps of making a primary incision; importing at least one surgical instrument head through the primary incision; making at least one secondary incision, smaller than the primary incision and the cross-section of the surgical instrument head, for a handle; extending the distal end of the handle through each secondary incision; attaching one of the surgical instrument heads to the distal end of the handle; manipulating the surgical instrument head with the handle to which it is attached; detaching the surgical instrument head from the handle; removing the surgical instrument head through the primary incision; and withdrawing the distal end of the handle from the secondary incision.

U.S. Pat. No. 6,723,043 to Kleeman et al. describes a surgical instrument assembly that includes an operative element and an insertion instrument removably engageable to the operative element. The insertion instrument is positionable in a patient with the operative element engaged thereto to position the operative element at an operative site in the patient. A transfer instrument is removably engageable to the operative element when the operative instrument is located at the operative site. The insertion instrument can then be removed. Methods for using the surgical instrument assembly are also disclosed.

SUMMARY OF THE INVENTION

In a broad aspect of some embodiments there is provided a laparoscopic system applicable for delivering, guiding and/or coupling an interchangeable laparoscopic end-effector (e.g., surgical tool) to a distal portion of a tool manipulator in a body cavity. Appropriately utilizing the system may constitute a shorter duration, reduced uncertainty and improved safety of procedure preparation and initiation.

In some embodiments, the interchangeable surgical tools are of regular laparoscopic size and are sequentially deliverable though a single regular laparoscopic port (usually between 5 and 10 mm in diameter). Once delivered into body cavity, each surgical tool may then be connected to a slender shaft manipulator having a diameter of 5 mm or less, optionally about 2 mm or less. The surgical tool may be connected to the manipulator distal end by a variety of interlocking means, including snap-lock mechanisms.

Optionally, a tool introducer may be used to position the interchangeable surgical tool in a chosen operation site within body before coupling to a tool manipulator. The introducer or manipulator distal end may have a pivoting connection to the surgical tool. An introducer pivoting distal end may be selectively angled by remote manipulation.

In some embodiments, at least one endoscope and/or camera may be introduced via the laparoscopic port to monitor surgical procedure and/or tool guidance and transfer between introducer and manipulator. An endoscope may have an angled or beveled tip for viewing the process of connecting between tool and manipulator. An endoscope/camera may be inserted through the port/trocar any time before or after the tool introducer is positioned there. In some embodiments, the laparoscopic system includes a special purpose monitoring endoscope: besides using a camera to monitor procedure as custom in laparoscopic procedures, a special purpose endoscope (which may be a standard/commercially available or specially designed endoscope) may be advanced via an introducer inner lumen for monitoring adaptor/interlocking operation. In some embodiments, a detachable mini-camera optionally in the form of a capsule or an end-effector is percutaneously introduced into the body cavity in a minimally invasive technique (e.g., using a tool introducer), and connected to a previously introduced tool holders (e.g., a distal end of a tool manipulator).

In some embodiments, the laparoscopic system includes an external guiding template indicating specific insertion ports for trocar and/or manipulators. Optionally, each port is specifically designed to guide a manipulator to a specific orientation within body for a rapid and accurate in-vivo coupling to an interchangeable end-effector. The operator may selectively choose between a fixed manipulator guiding, that is relevant for manipulator introduction into body and engaging with the effector, and a free manipulator movement, relevant for proper surgical intervention. A template frame may be procedure-specific and/or patient-specific (and allow all possible relevant ports) or adjustable according to need. It may be operated manually and/or remotely. Beneath or included in the template frame, there may be an adhesive sealant cloth and/or pad that provides adequate sealing around port/incision to avoid contamination and C02 leakage.

In some embodiments, the laparoscopic system includes a needlescopic manipulator supporting mechanism capable of setting a specific chosen position of a miniature element (e.g., effector or camera) within body. The supporting mechanism may be operated manually or robotically, and allow fixedly 3O orientation change of the miniature element manipulator/holder (slender shaft/handle). The supporting mechanism may be a truss-based mechanism or a ball-socket mechanism; may include a ratchet mechanism and may be implemented in the external guiding template, for example in or in association to at least one of its ports.

In some embodiments, the laparoscopic system includes a surgical tool vectoring mechanism selectively and/or automatically altering introducer distal end when/after the effector is protruding into body through the trocar, in order to facilitate accurate and rapid engagement with manipulator distal end. The vectoring mechanism may allow an accurate, timely direction shift of the surgical tool/effector with respect to tool-holder longitudinal axis. Optionally, the tool is detachable from the introducing tool holder, and is further connectable to a second tool holder (e.g., a manipulator) that is substantially parallel and/or collinear and/or concentric with respect to a receiving portion of the tool/adaptor after the said direction shift. The vectoring mechanism may be passive (e.g., using a spring/nitinol set to shift the tool to a predetermined direction), or active/adjustable (e.g., either mechanically—for example by maneuvering the introducing tool holder along the trocar path, or electronically/robotically—after the tool is completely protruding through the trocar).

Optionally, an end-effector may be coupled to manipulator using rapid interlocking means (e.g., snap locking means). In some embodiments, the laparoscopic system includes a "handoff" coupling mechanism, i.e., a double-action locking mechanism allowing secure passing between two end-portions of laparoscopic slender shafts (e.g., trocars, manipulators, introducers, etc.) whereby the effector is released from introducer only after interlocking with manipulator and vice versa. Optionally, a special tool removal device may be used for detaching an effector to/from a manipulator, or this may be performed by the tool introducer itself.

According to an aspect of some embodiments there is provided a system for positioning an interchangeable tool in a body cavity, the system comprising:

a channel comprising a lumen in direct communication with the body cavity;

a tool introducer comprising a longitudinal axis and a distal end, the tool introducer is capable of traveling through the channel lumen; and a tool holder covering at least a portion of the interchangeable tool, the tool holder is pivotally connected to the tool introducer distal end, thereby allowing angular positioning of the interchangeable tool after the tool holder emerges from the channel into the body cavity.

In some embodiments, the angular positioning is predetermined. Alternatively and/or additionally, the angular positioning is constant. Alternatively and/or additionally, the angular positioning is selectively chosen after the tool holder emergence into the body cavity.

In some embodiments, the interchangeable tool includes a passage for accommodating a distal portion of a tool manipulator. Alternatively and/or additionally, the angular positioning positions the passage with respect to the distal portion of the tool manipulator. Alternatively and/or additionally, the passage is concentric to the distal portion of the tool manipulator after the angular positioning.

In some embodiments, the interchangeable tool comprises one of the group consisting of a grasper, a dissector, a needle holder, scissors, a camera, an endoscope, a heat source, a sensing probe, a cryogenic probe, a dissector, a biopsy probe, a cutting tool, a laser source, an IR source, a light source, an illumination source, an ultrasound probe, an electrocautery device, a drug delivery device and combinations thereof.

In some embodiments, the system further comprising an external guiding device configured to guide a tool manipulator to engage the interchangeable tool in the body cavity, wherein the guiding device comprises:

a center guide comprising a first lumen adapted to accommodate the channel;

an adjustable peripheral guide having a proximal end connected to the center guide and a distal end incorporating a second lumen; wherein:

the tool introducer is distally connected to the interchangeable tool and readily deployed in the body cavity through the channel accommodated in the first lumen of the center guide; and the adjustable peripheral guide is adjusted to guide the tool manipulator through the second lumen to engage the interchangeable tool.

In some embodiments, the external guiding device is further adapted to guide a distal portion of the tool manipulator in a defined orientation and/or depth in the body cavity. Alternatively and/or additionally, the external guiding device is adapted to selectively lock the distal portion of the tool manipulator in the orientation and/or depth. Alternatively and/or additionally, the distal portion of the tool manipulator is concentric to an inner passage of said interchangeable tool.

In some embodiments, the second lumen includes a longitudinal axis that is angled towards the center guide in at least one dimension.

In some embodiments, the adjustable peripheral guide is adjustable by at least one of: lengthening, bending, tilting, rotating, deforming and/or any combination thereof.

In some embodiments, the interchangeable tool is tilted with respect to the tool introducer.

In some embodiments, the system further comprises an external frame comprising at least one external guiding device.

In some embodiments, the tool holder is a tool cartridge.

In some embodiments, the tool introducer comprises a tubular section. Alternatively and/or additionally, the tubular section further comprises an endoscope deployable in the tubular section. Alternatively and/or additionally, the tubular section includes a window, thereby enabling endoscopic visualization by the endoscope.

According to an aspect of some embodiments there is provided a method for engaging an interchangeable tool, the tool having an inner passage, with a distal portion of a tool manipulator in a body cavity, the method comprising the steps of:

inserting a tool introducer into a channel, the channel comprising a lumen providing direct communication into the body cavity and wherein a proximal end of said interchangeable tool is reversibly connected to a distal end of the tool introducer;

orienting the distal portion of the tool manipulator in the body cavity;

emerging the interchangeable tool from the channel into the body cavity; and positioning the interchangeable tool eccentrically to the lumen of the channel wherein the inner passage of the interchangeable tool is angled towards the distal portion of the tool manipulator.

In some embodiments, the positioning is automatically executed once the interchangeable tool entirely emerges from the channel. Alternatively and/or additionally, the positioning is selectively executed by an operator.

In some embodiments, the method further comprising predetermining an angle of the positioning of the interchangeable tool. Alternatively and/or additionally, the method comprising using a constant angle for the positioning of the interchangeable tool. Alternatively and/or additionally, the method further comprising selectively choosing an angle of the positioning of the interchangeable tool after emerging the interchangeable tool. Alternatively and/or additionally, the inner passage of the interchangeable tool is concentric to the distal portion of the tool manipulator after the positioning.

In some embodiments, the orientating step is accomplished by means of an external guiding device.

In some embodiments, the method further comprises the steps:

advancing the distal portion of said tool manipulator to engage with the inner passage of the interchangeable tool; and engaging the distal portion of the tool manipulator with the inner passage of the interchangeable tool. Alternatively and/or additionally, the method further comprising the steps of locating the distal end of the tool manipulator before introducing the interchangeable tool by:

introducing an elongated tool introducer through the lumen into the body cavity and moving the distal end of the tool introducer into a position adjacent to a position to which the distal portion of the tool manipulator is oriented and guiding the distal end of the tool manipulator to engage with the inner passage when the interchangeable tool is emerged into the body cavity and/or introducing an elongated channel, the channel comprising a lumen, into the body cavity and moving the distal end of the elongated channel into a position in the body cavity adjacent to a position to which the distal portion of the tool manipulator is oriented and guiding the distal end of the tool manipulator to engage with the inner passage when the interchangeable tool is emerged into the body cavity; and advancing the distal portion of tool manipulator to engage with the inner passage.

In some embodiments, the method and further comprising the step of capturing the distal end of the tool manipulator at an entry point of the tool manipulator as the distal end of the tool manipulator emerges into the body cavity and before the distal end of the tool manipulator moves substantially into the body cavity by utilizing the elongated tool introducer and/or the elongated channel having an lumen.

In some embodiments comprising monitoring the engaging procedure via an endoscope situated in a tubular section of the tool introducer.

In some embodiments, the interchangeable tool is housed in a tool holder.

In some embodiments, the first lumen is a laparoscopic port having a diameter that is equal or more than 5 mm. In some embodiments, the second lumen is a needlescopic port having a diameter that is equal or less than 3 mm. Optionally, the second lumen includes a longitudinal axis that is angled towards the center guide in at least one dimension. Optionally, the adjustable peripheral guide is adjustable by at least one of: lengthening, bending, tilting, rotating, deforming and/or any combination thereof. Optionally, the interchangeable tool is tilted with respect to the tool introducer.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 5A-F illustrate an exemplary interchangeable tools insertion system and steps of introduction thereof, in accordance with an exemplary embodiment of the present invention;

FIGS. 6A-B illustrate a side view and a corresponding top cut-view of a tool nested in an introduced cartridge, in accordance with an exemplary embodiment of the present invention;

DETAILED DESCRIPTIONS OF EXEMPLARY EMBODIMENTS

(a) Exemplary Rapid Laparoscopy System

Figure 1A:
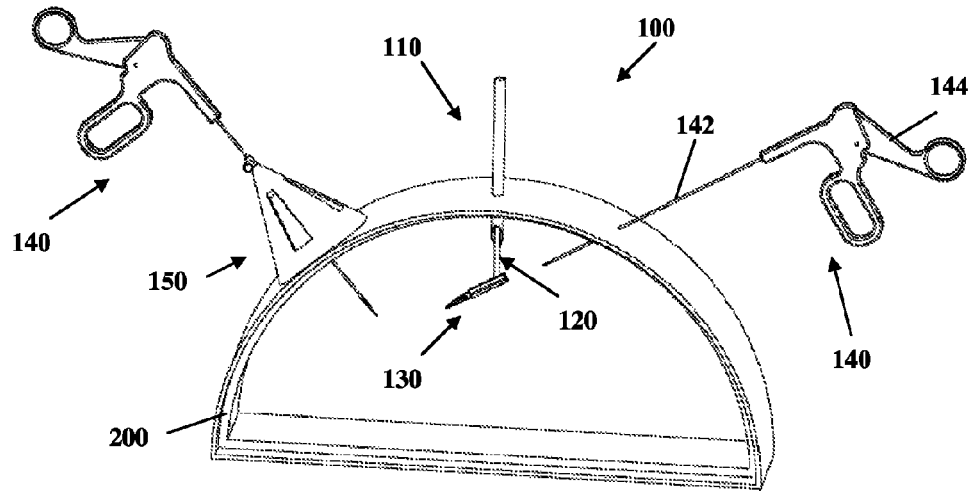
FIGS. 1A-B illustrate rapid laparoscopy system in operation, and a corresponding zoom-in portion, in accordance with an exemplary embodiment of the present invention.

FIG. 1 illustrate an exemplary rapid laparoscopy system 100 deployed in patient body 200 (shown in a "sliced" proportion for demonstrative purposes), the system includes an introducing sleeve 110 and at least one tool manipulator 140. In some embodiments, sleeve 110 is a trocar having a tubular body 112 and a substantially sharp or blunt distal end that is capable of channeling a surgical tool 130 into a cavity within body 200 using a tool introducer 120. Sleeve 110 may be of any preferred size, and usually between 3 to 20 mm in diameter, optionally 5 to 10 mm (e.g., similar in size to regular laparoscopic port). Sleeve 110 may be sized (e.g., smallest cross section) to accommodate a largest of tools 130 in a specific tool kit. In some embodiments, system 100 includes a single regular-sized laparoscopic port that may be utilized for tool(s) 130 insertion into body and/or connection to manipulator(s) 140.

Figure 1B:
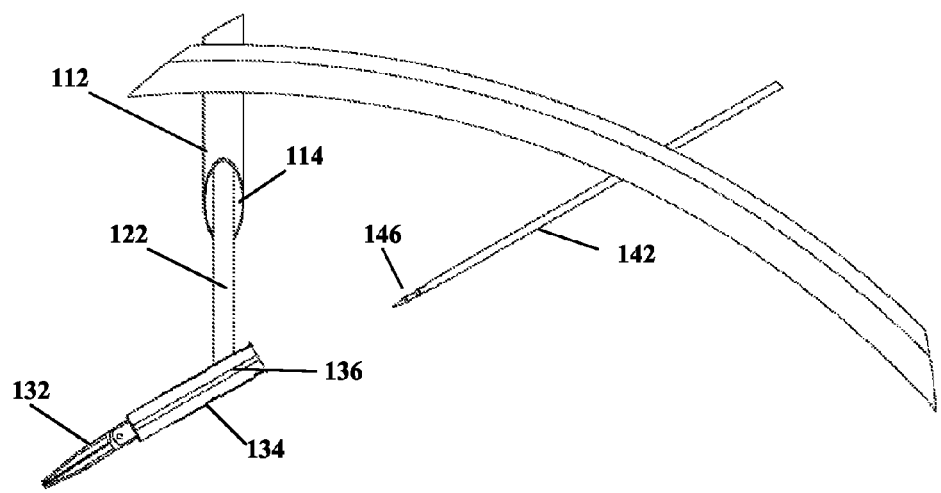

Tool 130 may be any operational element (e.g., a probe or an instrument) deployable within a body, including but not limited to: surgical tools, grasping elements, dissectors, needle holders, clippers, scissors, connecting (e.g., stapling) elements, biopsy related instruments, sensor elements, imaging elements, clamping or grasping devices, heat generating probes (including RF, laser, IR, light, etc.), cryogenic probes, cutting and dissecting devices or energy sources, ultrasound probes, etc. In some embodiments, tool 130 is interchangeable and may be releasably attached to a distal tip 146 of manipulator 140, as shown in FIG. 1B. In some embodiments, tool 130 includes a tool head or effector 132 (e.g., grasping means as presently illustrated), a body 134 and an inner passage 136 for accommodating a manipulator distal tip 146. In some embodiments, tool 130 further includes locking mechanism (not shown) that allows safe coupling to manipulator 140.

In some embodiments, introducer 120 includes a tubular body 122, with an optional distal projection (optionally, tail-like), that is associated with (e.g., connected to, for example by using a Babcock grasper) tool 130. In some embodiments, tool introducer 120 is releasably connected to tool 130 and/or to any sort of adapter or cartridge 124 (shown in FIG. 5) that may be associated with (e.g., connect to or contain) tool 130 until deployment and/or operation. In some embodiments, introducer 120 allows a defined 3O orientation of tool 130 within body, thus providing a simpler and a potentially rapid approach for engaging manipulator 140 with inner passage 136 of tool 130. Optionally, tool 130 orientation is selectively chosen, optionally adequately accurate. Optionally, tool 130 is oriented to a specific predefined position, for example by using a pivoting mechanism that combines spring energy and motion limiting (not shown). Alternatively or additionally, tool orientation is achieved by manual or computerized operation, either remotely or at site. In some embodiments, introducer 120 and/or any associated tool holder, adapter or cartridge, further includes a safe tool passing mechanism (not shown), optionally a "handoff" type mechanism, which allows release of tool 130 only after the latter is safely interlocked with manipulator 140, and optionally vice versa.

In some embodiments, manipulator 140 includes a shaft 142, distal tip 146 and a tool operating handle 144. Shaft 142 and tip 146 largest cross section may be 0.5 to 5 mm in diameter, optionally 1 to 2.5 mm, optionally about 1 mm, about 1.5 mm or about 2 mm or higher or lower or intermediate. Tip 146 is optionally sharp and/or pointed in order to allow at least one of tissue penetration and easier engagement into tool inner passage 136. Optionally, tip 146 is a Veres needle which optionally permits penetration through skin and abdominal wall tissue while preventing injury of internal organs (e.g., bowels), when not "armed". Optionally, tip 146 includes interlocking means, e.g., threading or a groove for snap-locking (not shown), for firmly connecting with tool 130. Handle 144 may be any manually operated type laparoscopic instrumentation handle or may be replaced with any robotic or other non-manually operated arm. In some embodiments, handle 144 includes mechanisms which operates tool 130 and/or their association (e.g., locking or releasing modes or operations).

At least part of the instruments are made from rigid biocompatible materials as known to a person skilled in the art, and may include stainless steel, optionally hardened or reinforced by carbon coating or fibers, ceramic materials, plastic/polymeric materials (e.g., PEEK), composite materials (e.g., carbon-epoxy), or any combination thereof.

In some embodiments, rapid laparoscopy system 100 further includes at least one, and preferably at least two, intraoperative imaging devices (e.g., microcameras and/or endoscopes), at least one of which can be used to monitor tool 130 transfer, locking and/or handoff from introducer 120 to manipulator 140, and optionally vice versa. Optionally, tool handoff monitor is an endoscope 128 (as shown in FIG. 5) located within or adjacent to trocar 110 and/or introducer 120. Additionally or alternatively, a grasped microcamera is transferred into body via trocar 110 using introducer 120 and then handed over to one of manipulators 140 which locates it in a preferred position to monitor the surgical operation. Other microcameras and/or endoscopes may be deployed in other locations using different manipulators.

In some embodiments, manipulator 140 is supported with an external holding device 150 which allows selective locking of manipulator in a certain positioning. This may be especially advantageous for example when a physician chooses to fixate a tool (e.g., a grasper) in a certain position while avoiding any unnecessary movements for a chosen period of time, and/or when he needs to occupy his hands with other manipulator(s). Holding device 150 may use a manipulator shaft grasper associated with a locking and/or guiding elements (not shown), thereby allowing selective alternating between a free movement mode and a position locking/guiding mode.

Figure 2:
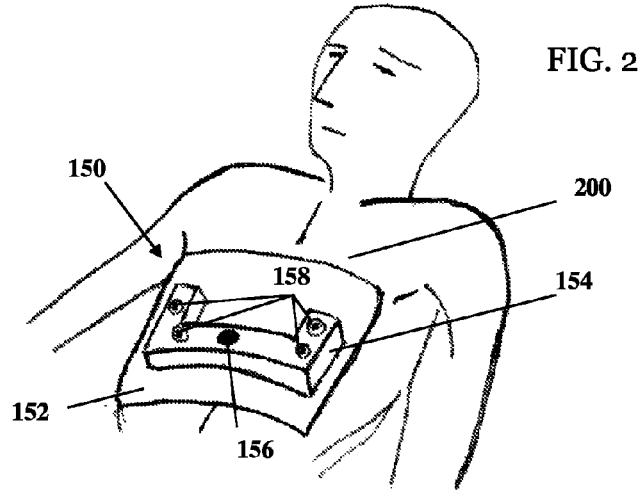
FIG. 2 illustrates a rapid-laparoscopy external template, in accordance with an exemplary embodiment of the present invention.

Reference is now made to FIG. 2 showing patient body 200 setting prior to a rapid laparoscopy procedure using an exemplary external holding device 150 in a form of template. In some embodiments, device 150 includes a template frame 154, a single tool introducer opening 156 and a plurality of manipulators openings 158. Frame 154 includes several extensions upon which laparoscopic instrumentation may be supported, the extensions may be provided in a predefined design according to a specific instrumentation allocation pattern (as derived from a specific surgical method) or may be assembled or manipulated (e.g., manually, electronically or other) to a different chosen arrangement.

Frame 154 may have a curved base for improved fitting over patient body 200 and/or may include fastening elements (not shown), such as fastening belts, for a firmer connection to patient body 200. Frame 154 may be made from any rigid or semi-rigid material, including metals, plastics and polymers.

External holding device 150 may include introducer-manipulators coordinating means which allow accurate manipulator engagement with a tool-head within body by guiding the manipulator in a specific correlated angle, plane and/or depth with respect to the tool head.

Exemplary holding device 150, as specifically illustrated in FIG. 2, is adapted for a single-port micro-laparoscopic procedure in which a single regular-sized laparoscopic port is used for delivering regular-sized laparoscopic instrumentation into body to be assembled to and operated with micro-sized, "needlescopic", manipulators. Accordingly, in some embodiments, tool introducer opening 156 is approximately 5 to 15 mm in diameter (although it may be changed to or replaced with to different sizes according to need) in order to allow regular sized tools and endoscope(s) as accustomed in "classic" laparoscopy approaches. Furthermore, in some embodiments, manipulators openings 158 are approximately 1 to 2.5 mm in diameter in order to allow needlescopic manipulation of tools within body with substantially lessened scarring effect of body 200.

Exemplary holding device 150 may include or be provided with a sealing pad or sheath 152 that may be especially useful in order to seal any entrapped gaseous substances (e.g., $CO_2$) within cavity of body 200, and/or for protecting against any potential contamination as may be resulted in case of directly communicating with open air. Sealing pad 152 may be made from any relatively pliant or elastic material such as soft polymer or silicone, while maintaining re-sealing capabilities when pierced with a micro-sized element, such as a needle (similarly to a septum seal).

Figure 3A:
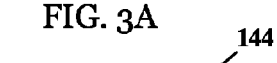
FIGS. 3A-H illustrate several deployment possibilities of a rapid-laparoscopy external template, in accordance with an exemplary embodiment of the present invention.
Figure 3A:
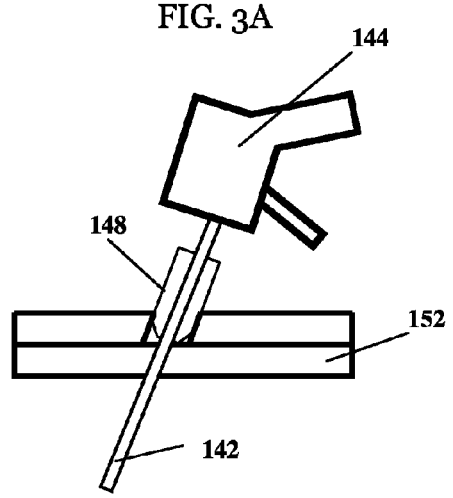
Figure 3B:
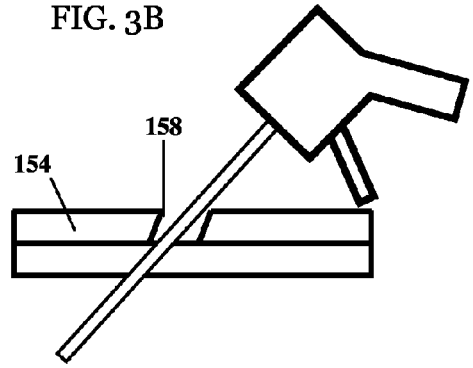
Figure 3C:
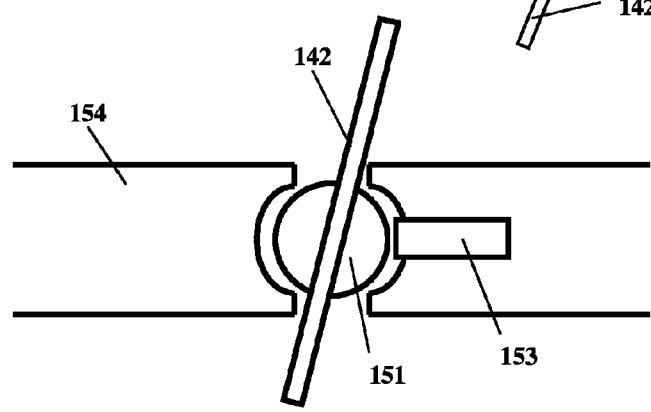
Figure 3D:
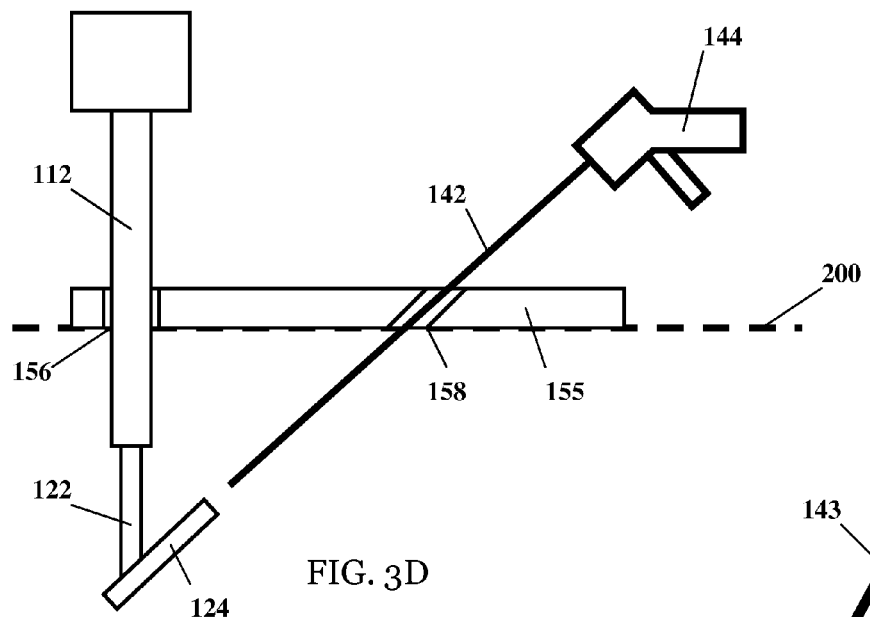

Device 150 may serve as a needle introducer template using specific pre-set orientation means. This may be advantageous especially for rapid location and handoff of tool 130 from introducer 120 to manipulator 140, as device 150 may be used to guide manipulator distal tip 146 adequately accurately towards tool inner passage 136. An exemplary pre-set orientation means are illustrated in FIGS. 3A-B, in which tool manipulator 140 is operated through manipulator opening 158 and a portion of sealing pad 152. As shown in FIG. 3A, a needle guiding element 148 is placed over a portion of shaft 142 and maintains a specific orientation according to a preformed design of opening 158. Optionally, guiding element 148 is a sleeve, optionally a splitting sleeve, and is made of a relatively rigid material, such as metal, plastic or polymer. After tool 130 is connected to manipulator distal end 136 and released from introducer 120, guiding element 148 may be removed and manipulator can be freely maneuverable as illustrated in FIG. 38. FIG. 3C illustrates a different type of an exemplary external supporting and/or guiding mechanism for manipulator 140 that includes a socket and a ball 151 design. Manipulator shaft 142 is passed through a lumen in ball joint 151 and allowed to freely move. Manipulator shaft 142 may be selectively paused in a specific orientation by deploying ball-joint lock 153.

Figure 3H:
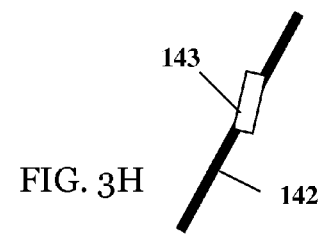

Reference is now made to FIG. 3O-H schematically illustrating possible applications of external holding device 150 having a template arm 155. In some embodiments, template arm 155 is applied for coordinating a rapid and accurate engagement of manipulator shaft 142 distal end and a tool coupled to cartridge or any other coupling element 124 that is angularly connected to introducer body 122. In some embodiments, the engagement coordination includes guiding at least two members in body to a specific point and a specific angle in a 3O coordinate system within body 200 in order to allow the rapid and accurate engagement. In some embodiments, template arm 155 includes at least one introducer path 156 and at least one manipulator path 158 that are located in the same plane, optionally a perpendicular plane (e.g., a sagittal plane or a transverse plane) of patient body 200, optionally an anterior or a posterior plane. In some embodiments, at least one of introducer path(s) and manipulator(s) path(s) are at least partially circular thereby allowing a relative rotation of circular shaft therein. Additionally or alternatively, at least one of the paths includes a specific mating pattern (not shown), for example a recess, a protrusion or any non-axisymmetrical shape, thereby allowing sliding of a shaft therein, the shaft having a mating cross section in a specific predetermined sliding plane into body.

FIG. 3O illustrates a template arm 155 having a single introducer path 156 and a single manipulator path 158, that are angled one with respect to the other in a same plane. In some embodiments, trocar body 112 is inserted through introducer path 156 thereby channeling introducer body 122 into patient body 200. In some embodiments, introducer body 122 is coupled to an interchangeable tool (not shown) via a tool coupling element 124 that takes an angular orientation with respect to introducer body 122 when it is completely emerged in body 200 through trocar body 122. In some embodiments, manipulator shaft 142 is inserted through manipulator path 158 and travels into body 200 in an angled orientation towards coupling element 124. In some embodiments, coupling element 124 (and/or a tool coupled to and/or an inner passage of the tool) are in same angle and same plane as manipulator shaft 142 when are inserted through paths 156 and 158, respectively, of template frame 155. In some embodiments, at least one of paths 156 and 158 includes a guiding slot, recess, projection, etc. (not shown) that necessitates tool-manipulator engagement in same point and/or angle and/or plane within body 200. Additionally or alternatively, markings are used to allow instruments manipulation within body to the desired tool-manipulator orientation.

Figure 3E:
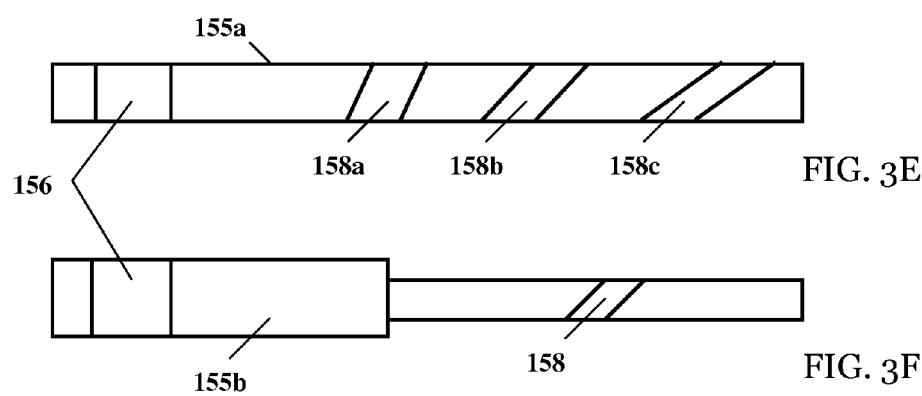
Figure 3F:
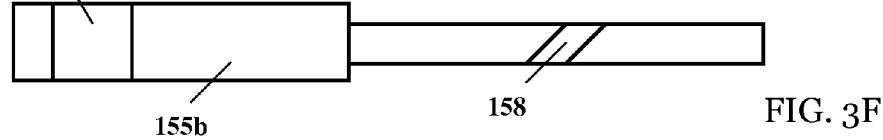
Figure 3G:
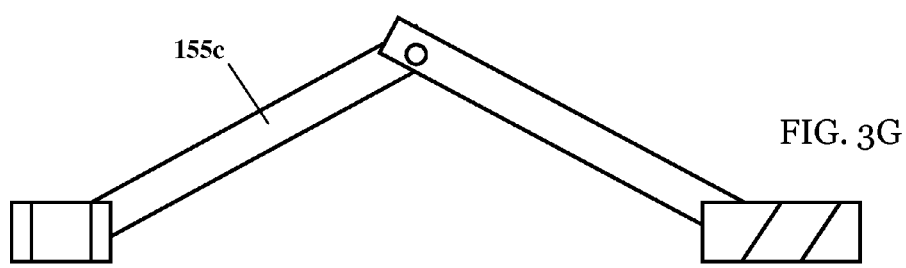

In some embodiments, template arm 155 is rotational around path 156 in order to allow penetration points of same or different manipulator(s) shaft(s) 142 around said rotational axis. FIGS. 3E-3G suggest different template arms 155a, 155b and 155c, which further allow penetration ports at different lengths along its longitudinal axis. In this way, an operator may use a single template arm to insert a plurality of manipulators at different penetration ports (e.g., as illustrated in FIG. 4B) which are located in different angles and lengths with respect to tool introducing port 210b.

FIG. 3E illustrates a template arm 155a having a single introducer path 156 and a plurality of manipulator paths, in this case three manipulator paths 158a, 158b and 158c. In some embodiments, at least some of the manipulator paths are angled in such a way that manipulator passing therethrough will engage a tool in the same depth but in a different angle (so at least two paths will have different angles) or in a different depth but in the same angle (so at least two paths will have same angles), or any combination thereof. FIG. 3F illustrates a template arm 155b having a single introducer path 156 and at least one, optionally a single, manipulator path 158. In some embodiments, template arm 155b has at least two pats, a first part that includes path 156 and a second part that includes path 158, that are telescopically connected, thereby allowing a selective distance alternation between the two paths.

FIG. 3G illustrates a template arm 155c having a similar approach to arm 155b, but uses at least two members jointly coupled to allow a selective distance alternation between introducer path 156 and manipulator path 158.

In some embodiments, for example when a template arm having a single manipulator path 158 is used, an operator may still choose a path angle. In some embodiments, path 158 is angled, either automatically or manually, using a mechanism (not shown) which correlates the distance between paths 156 and 158 and/or the depth of tool coupling element 124 and/or the angle of coupling element 124. Alternatively or additionally, manipulator insertion angle may be altered while using a constant manipulator path 158 angle, using angle adaptors 143 that are assembled (permanently or detachably) to a portion of manipulator shaft 142 (as illustrated in FIG. 3H).

(b) Exemplary Micro-Laparoscopy Approach

The present invention will provide descriptions for laparoscopic cholecystectomy procedures, although it should be clear that the proposed treatment and medical tools can be applied in many different minimally invasive and/or anterior and/or endoscopic surgical procedures.

Figure 4A:
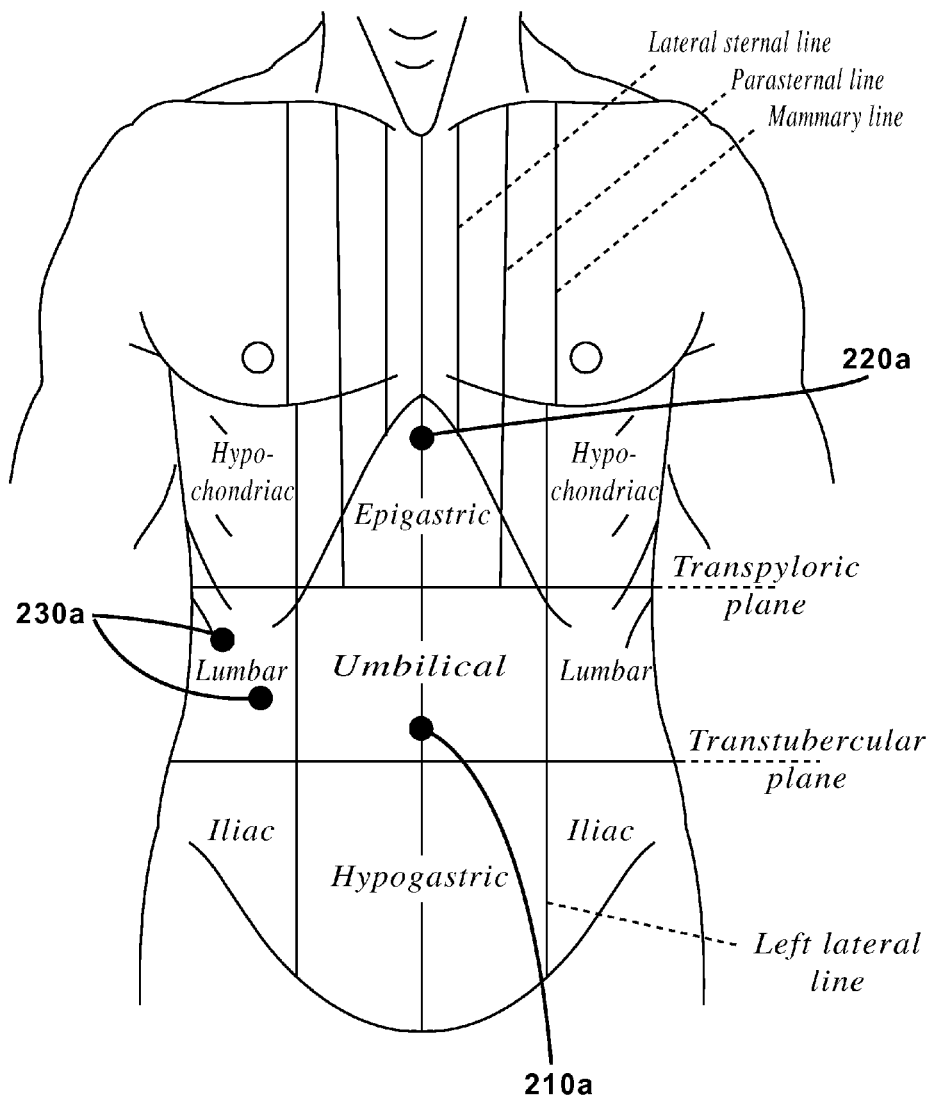
FIGS. 4A-B illustrate exemplary prior-art and an optional laparoscopic ports schemes, in accordance with an exemplary embodiment of the present invention.
Figure 4B:
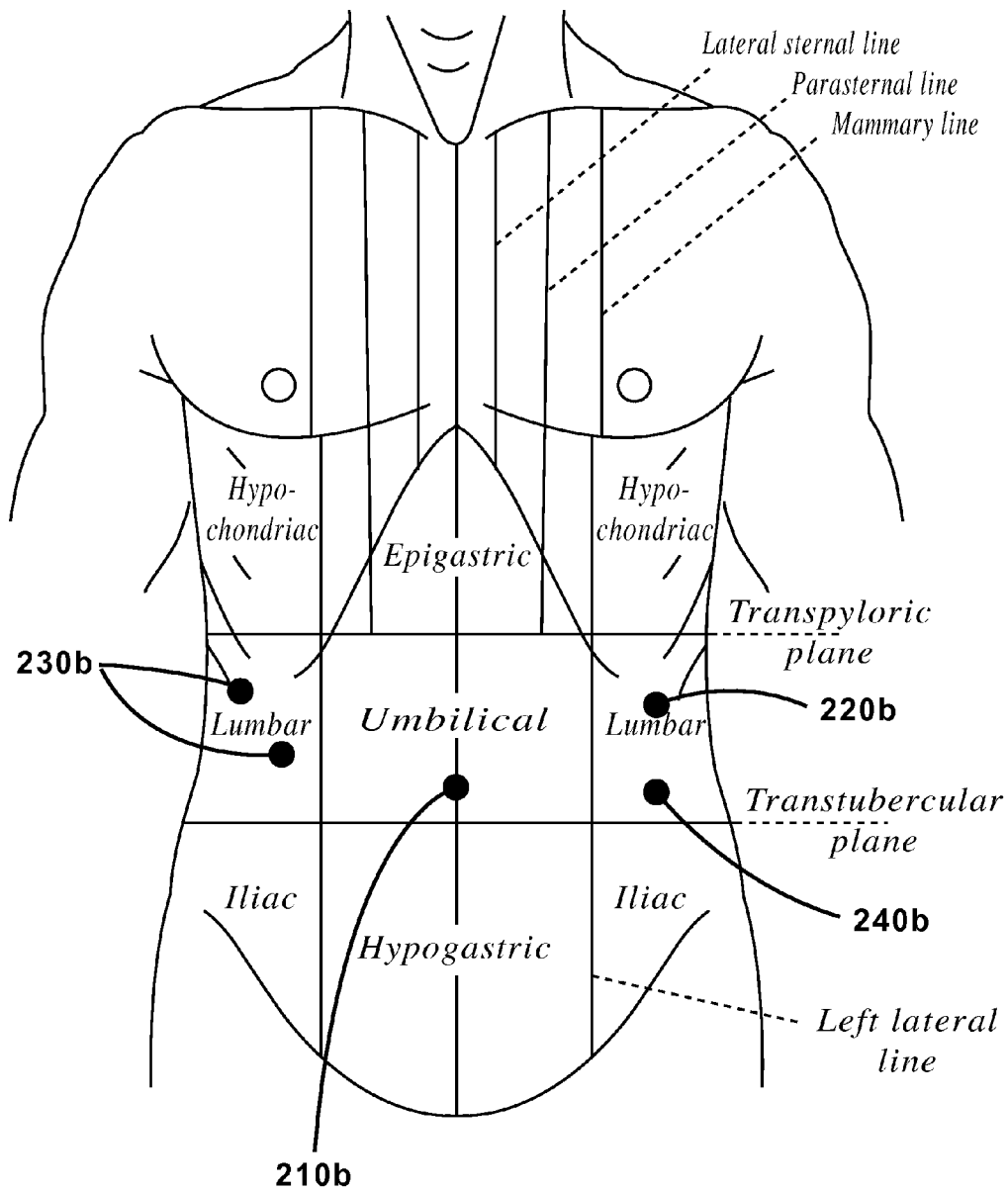

FIG. 4A illustrates a prior-art laparoscopic cholecystectomy procedure which utilizes a minimal sum of four laparoscopic ports:

(1) An endoscope port 210a of approximately 10 mm in diameter, usually located at patient's umbilicus. Port 210a allows insertion of a trocar by which an endoscope may be inserted into body;

(2) A main operating port 220a, approximately 10 mm in diameter, usually located below the sternum. Port 220a allows insertion of different types of surgical and other instruments, for example tools for suction, clipping, dissecting, cutting and hooking;

(3) Two graspers ports 230b, approximately 5 mm in diameter each, usually located adjacently below the right-lateral ribs. Commonly, two graspers are delivered through ports 230b to grasp and hold the gall bladder in a certain position prior to executing surgical intervention steps.

In a normal laparoscopic cholecystectomy, the abdomen is first inflated with $CO_2$ via a 2.5 mm special-purpose Veres-needle, followed by opening of ports 210a, 220a and 230a. An endoscope is then inserted through port 210a. After the abdomen is thoroughly scanned, graspers are introduced through ports 230a. A first grasper grasps the gall bladder at the Fundus region and then stretches and pushes it over the liver. A second grasper grasps the gall bladder at the Infundibulum region to maneuver it laterally towards abdomen walls, thereby uncovering the cystic duct and the cystic artery. Several surgical instruments are then serially introduced via port 220a. At first, a dissector is used to separate between the cystic duct and artery, a clipper is then introduced to block inflow of duct and artery, later to be both cut by scissors. Finally, the gall balder is separated using hooks or scissors and removed from patient body through port 210a (either as a whole or in pieces).

The use of a combined single-port laparoscopy and needlescopy approaches, allows the surgeon more flexibility in choosing a laparoscopic ports scheme that may be procedure-specific and/or patient-specific. For example, the use of slender manipulators allows more flexibility in choosing a number of manipulators and associated tools to be applied simultaneously or in sequence while optionally covering larger or smaller operated regions. Furthermore, more imaging and/or illumination sources may be introduced and operated at different regions within abdomen, thus allowing improved visual monitoring of procedure and tool handling within body. Once a camera is situated within body (e.g., via a needlescopic port) and abdomen cavity is adequately monitored, an endoscope may be considered unnecessary or be pulled in and out the single laparoscopic port for sequential tools introductions into the abdomen through this port.

FIG. 4B illustrates an optional exemplary porting scheme for laparoscopic cholecystectomy, which may be advantageously utilized using a rapid micro-laparoscopy approach of the present invention:

(1) A tools introducing port 210b of approximately 10 mm in diameter, usually located at patient's umbilicus. Port 210b allows insertion of a trocar by which tools (e.g., tools 130) may be sequentially inserted into body optionally followed by an endoscope. The 10 mm port may serve to introduce regular size instruments such as clippers, Ligasure/harmonic scalpel, suction, electrosurgical hook, etc.;

(2) At least one camera port 220b of approximately 1 mm in diameter, usually located adjacently below the left-lateral ribs. A micro-camera (sized 1 to 10 mm in diameter) may be inserted though port 210b using a tool introducer (e.g., introducer 120) and transferred to a manipulator that is operated and/or protruding through port 220b. Alternatively or additionally, an even smaller camera (sized 1 mm or less) may be delivered into body directly though the 1 mm incision of port 220b;

(3) At least two graspers' ports 230b of approximately 2 mm in diameter each, usually located adjacently below the right-lateral ribs. Similarly to the micro-camera, the graspers may be delivered through port 210b and connected to manipulators protruding through ports 230b.

(4) Optionally one or more illuminator ports 240b for holding illumination source, such as LED illumination, IR light, regular light, fiber optics etc. Port 240b is approximately 1 mm in diameter and located adjacently to port 220b, also below the left-lateral ribs. This may be especially useful in case that the mini-camera does not include indigenous illumination capabilities, for example in view of the importance to minimize its size.

In some embodiments, similarly to normal laparoscopic cholecystectomy, the abdomen is first inflated with C02 using a 2.5 mm special-purpose Veres-needle. Camera and illumination manipulators are then introduced through 1 mm incisions made as ports 220b and 240b, respectively. Port 210b is then opened and a trocar is introduced. An interchangeable mini-camera and illumination are then introduced via the trocar at port 210b and connected to corresponding manipulators distal ends protruding at ports 220b and 240b. Two 5 mm sized interchangeable graspers may then be introduced via port 210b and connected to corresponding manipulators distal ends protruding at ports 230b. The rest of the surgical procedure steps may be carried out as in the prior art approach previously described, while "regular" laparoscopy instruments are inserted to abdomen and manipulated via port 210b. Alternatively, at least one interchangeable surgical tool replaces a "regular" laparoscopy instrument and delivered to abdomen cavity later to be connected to a corresponding needlescopic manipulator that is located at a special purpose port (not shown) according to need and/or surgeon choice.

In some embodiments, an external holding device or template 150 is used for any of the purposes previously described, whereas a specific template frame 154 design and/or template frame 155 are chosen and/or assembled at-site according to the requested laparoscopic porting scheme.

(c) Exemplary Deployment of a Rapid Micro-Laparoscopy System

Reference is now made to FIGS. 5A-F illustrating an exemplary rapid micro-laparoscopy system 100 and steps of introduction of tools therethrough. For demonstrative purposes, in FIGS. 5A-C a tool itself is not illustrated.

In some embodiments, after deployment of system 100 as previously described, a trocar 110, having a tubular body 112 of about 10 mm in diameter, is introduced through port 210b thereby allowing a safe passage of laparoscopic tools and instrumentation into body. Optionally, an introducer 120 having a body 122 of about 5 to 9 mm in diameter is inserted through trocar 110. Optionally, body 122 is tubular with an inner diameter of equal or less than 8 mm, optionally about 5 mm, and allowing insertion therethrough of endoscope 128 which is about 8 mm or less in diameter. In some embodiments, endoscope 128 is a side-vision endoscope having a lens 129 projected through a special lateral opening 127, and can provide monitoring for the tool exchange within body via lateral window(s) 125 of body 122. Body 122 includes a distal end 126 that is pivotally connected to tool cartridge 124 currently illustrated without a tool for demonstrative purposes.

Phase A of a tool delivery is illustrated in FIG. 5A where an assembly of introducer body 122, endoscope 128 and cartridge 124 are traveled within trocar body 112 lumen towards abdomen cavity.

Phase B of tool delivery is illustrated in FIG. 58 where cartridge 124 almost entirely protrudes out of trocar 110 lumen. Tool introducer distal end 126 including lateral window 125 also protrudes, so endoscope monitoring may be initiated.

In Phase C (FIG. 5C), cartridge 124 is oriented with respect to the longitudinal axis of trocar-introducer assembly after entirely protruded into body cavity. In some embodiments, a released potential energy based device (e.g., a released spring motion; not shown) is used for a passive cartridge 124 altering to a specific, optionally predefined orientation, optionally further using any orientation control mechanism (such as a motion limiter, a designated cam, an electronic control element, etc.). Alternatively or additionally, cartridge 124 alternation is actively performed either manually or remotely via a robotic arm. In some embodiments, cartridge 124 and/or the encapsulated tool longitudinal axis are substantially parallel or concentric to manipulator shaft 146, thereby allowing a rapid engagement and connecting therebetween, as suggested in phase D (FIG. 50).

The last delivery phase E (FIG. 5E) takes place once or after tool 130 is appropriately connected to manipulator shaft 146. In a first embodiment, two distinct locking mechanisms (not shown) are situated in cartridge 124 and/or tool 130 and are used for locking the tool to cartridge 124 and to manipulator shaft 146, respectively. In a second embodiment, the two locking mechanisms are interrelated in a way that when a first lock is in locked mode the second lock is in released mode, and vice versa, thus allowing a "handoff" passing of the tool in a secure way.

Once phase E is complete, and tool 130 is connected to manipulator 140 and disconnected from introducer 120, the tool may be utilized to its designated task. In case that an external template 150 is used for guiding manipulator shaft 146 towards tool 130, the guiding element (e.g., guiding sleeve 148) may be released or removed, thereby allowing relatively free movement of manipulator shaft 146.

(d) Exemplary Tool Handoff Delivery

Reference is now made to FIG. 6 that illustrate a side view and a corresponding top cut-view of an exemplary tool 1300 nested in an exemplary cartridge 1240 that is connected and/or part of an exemplary tool introducer 1200 having a body 1220. An exemplary needlescopic manipulator shaft 1400 is proximately distant and optionally concentric to tool 1300 suggesting an initial pre-connecting phase (e.g., phase C as previously described).

In some embodiments, cartridge 1240 is pivotally connected to introducer body 1220 with a pivot 1210 thereby allowing at least partial rotation around pivot 1210 axis. Optionally, cartridge 1240 rotation is accomplished using a spring mechanism (not shown) or by any other means known to art. Optionally, a desired 30 cartridge/tool orientation is accomplished by maneuvering cartridge 1240 from outside patient body, either manually or remotely.

In some embodiments, tool 1300 is an interchangeable grasper having a head 1320, body 1340 and an inner passage 1360 capable of telescopically accommodating a distal tip of manipulator 1400. Optionally, grasper 1300 is approximately 5 mm in diameter. In some embodiments, for example as illustrated in FIG. 6, only grasper head 1320 is encapsulated by cartridge 1240, within cartridge tool head housing 1242, whereas at least part of grasper body 1340, optionally most or all its length, extends outwardly within body cavity. Cartridge 1240 may further include a tool grasper 1270 for locking grasper head 1320 within housing 1242 or selectively releasing it when deployed.

Figure 7A:
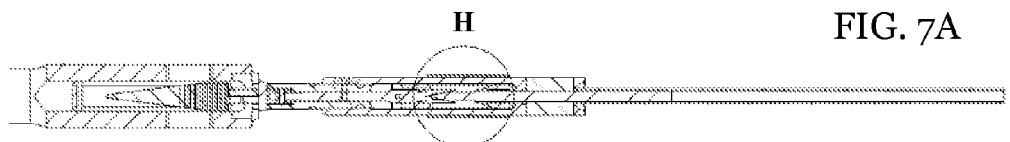
FIGS. 7A-C illustrate several interlocking possibilities to a tool, in accordance with an exemplary embodiment of the present invention.

Reference is now made to FIG. 7A illustrating a top cut-view of grasper 1300, having a tubular frame 1342, nested in cartridge 1240 while interlocked with a manipulator distal tip 1460. Optionally, tool 1300 includes a beveled tool opening 1362 for an easier accommodation of manipulator distal tip 1460. In some embodiments, tool 1300 includes a manipulator tip lock 1370 situated along a portion of inner passage 1360, for snap-locking to a distal tip of manipulator 1400, using a lock beveled opening 1372 and a lock narrow section 1374 which is designed to mate with a corresponding recess 1462 located proximally to manipulator tip 1460. In some embodiments, tip lock 1370 is connected at its proximal side to a tool inner shaft 1380 and is blocked from moving distally by a releasing mechanism lock widener 1394 shown in FIG. 7 in a locking position. In some embodiments, lock widener 1394 has a rounded portion 1396 for an optional selective smoother proximal travel within lock beveled opening 1374. In some embodiments, lock widener is coupled to a releasing mechanism outer sleeve 1392 that is rotatable around tool body tubular frame 1342.

Figure 8:
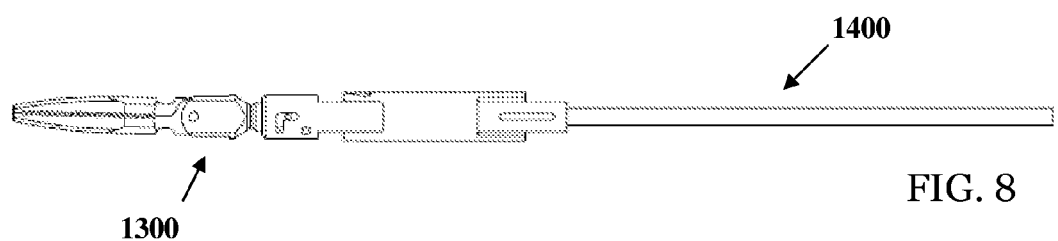
FIG. 8 illustrates a side view of a tool connected to manipulator, in accordance with an exemplary embodiment of the present invention.

When locked to manipulator 1400, grasper 1300 may now be released from tool cartridge 1240 as illustrated in FIG. 8. In some embodiments, when grasper 1300 is distally pulled (e.g., by manipulator 1400) it easily disconnects from cartridge 1240 by laterally widening cartridge tool grasper 1270 during pullout. Optionally, a threshold force is required for achieving disconnection in order to avoid unintentional tool escapes from cartridge grasping.

Figure 7B:
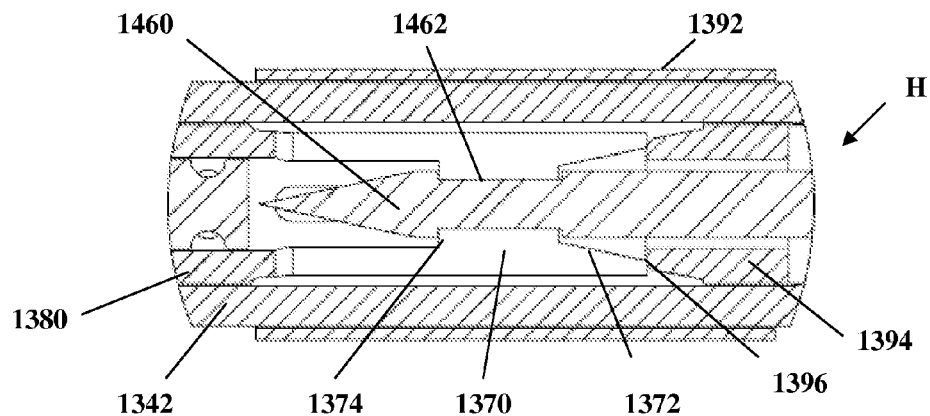
Figure 7B:
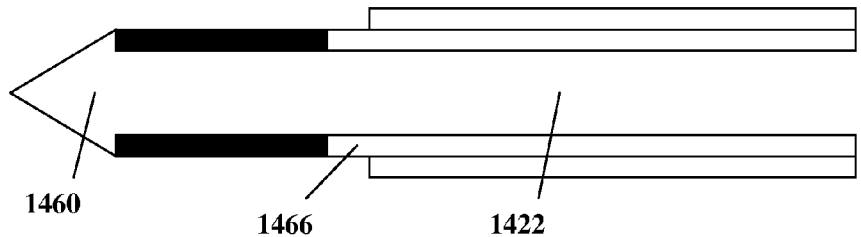
Figure 7C:
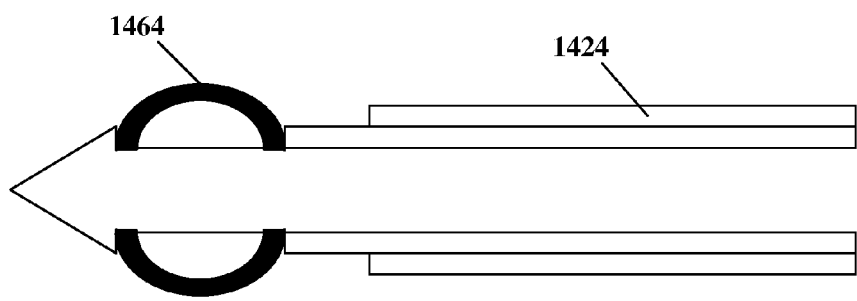

Additionally or alternatively, grasper release is achieved by unlocking a second locking mechanism that releasably holds it within cartridge housing 1242. FIGS. 7B and 7C illustrate another exemplary design for manipulator 1400 in unlocked and locked modes, respectively. In some embodiments, manipulator 1400 includes an inner shaft 1422 having a distally pointed end 1460, an intermediate sleeve 1466 having a distal compressible portion 1464 and optionally maintains substantially same outer diameter with shaft 1422 maximal diameter, and an outer sleeve 1424. In some embodiments, compressible portion 1464 expands and/or send arms when compressed, thereby produced interlocking when engaged into a recess in a smaller diameter lumen. Optionally, compressible portion 1464 includes a tubular portion that is elastic and/or braided and/or slitted and/or bellowed (i.e., includes bellows). Optionally, compressible 1464 includes a stent-like design, optionally a cage-like design, optionally includes at least one strip that is bendable to an arch. Optionally, outer sleeve 1424 is connectible to tool 1300 and allows rotatability to an inner rotatable part and/or a sliding movement of an inner slidable part of tool 1300. Optionally, outer sleeve rotates and/or slides with respect to shaft 1422 and/or intermediate sleeve 1466 thereby allowing operation of tool 1300 and/or locking/unlocking modes shift. Optionally, locking and unlocking are achieved by relative movement of shaft 1422 and intermediate sleeve 1466 (e.g., by pulling or pushing sleeve 1466 proximal end).

(e) Exemplary Tool Removal

Figure 9:
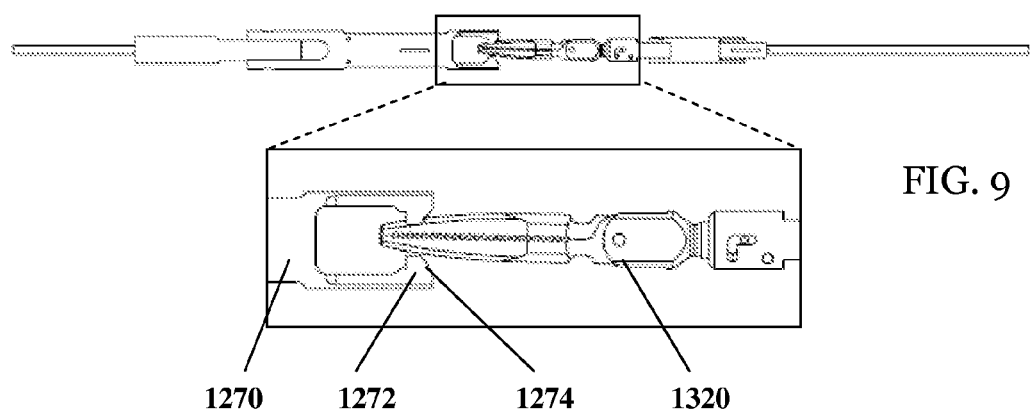
FIG. 9 illustrates a side view of a tool connected to a manipulator pressed against a tool cartridge, in accordance with an exemplary embodiment of the present invention.

In some embodiments, after final utilization of a tool and/or at procedure termination the tool should be disconnected from its corresponding manipulator 1400 and be safely removed from body via tool introducing port 210b. Optionally, special removing device and/or tool grasping cartridge are used (not shown). Alternatively, same instrumentation is used in a substantially reverse order for tool(s) removal. Reference is now made to FIG. 9 illustrating a side view of grasper 1300 connected to manipulator 1400 while pressed against cartridge 1240. In some embodiments, cartridge tool grasper 1270 includes a tool opening teeth 1272 including beveled end portions 1274 allowing tool grasper widening when grasper head 1320 is pressed against it with a force that exceeds a defined threshold force.

Now that grasper 1300 is re-nested in cartridge 1240 a second mechanism is operated for releasing the grasping of manipulator tip 1460 and disconnecting from manipulator 1400, as illustrated FIG. 10. In some embodiments, releasing mechanism outer sleeve 1392 includes a diagonal slot 1397 that is engaged with a pin 1398 laterally projecting from tool body inner shaft 1380. Optionally, outer sleeve 1392 and inner shaft 1380 can slide and/or rotate one with respect to the other, so that pin 1398 travel from a first corner (position 11 in FIG. 10C) to a second corner (position 12 in FIG. 10D) of diagonal slot 1397 is accomplished by a proximal partial sliding of inner shaft 1380 and its rotation counter-clockwise partial rotation with respect to outer sleeve 1392.

In some embodiments, tool body tubular frame 1342 includes an L-slot 1344 that is engaged with a pin 1382 laterally projecting from tool body inner shaft 1380. Optionally, tubular frame 1342 and inner shaft 1380 can slide and/or rotate one with respect to the other, so that pin 1382 travel from a first corner (position J1 in FIG. 10C) to a second corner (position J2 in FIG. 10D) of L-slot 1344 is accomplished by a proximal partial sliding of inner shaft 1380 and its rotation counter-clockwise partial rotation with respect to tubular frame 1342.

Figure 10A:
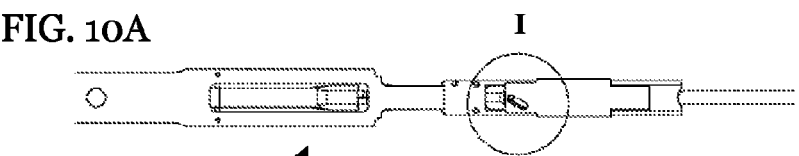
FIGS. 10A-F illustrate several regular and cut views of tool interlocking with a cartridge and release from a manipulator, in accordance with an exemplary embodiment of the present invention.
Figure 10B:
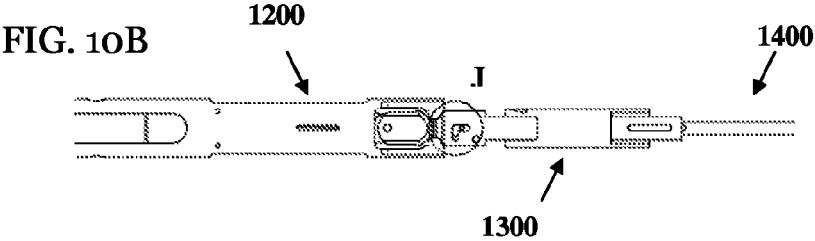
Figure 10C:
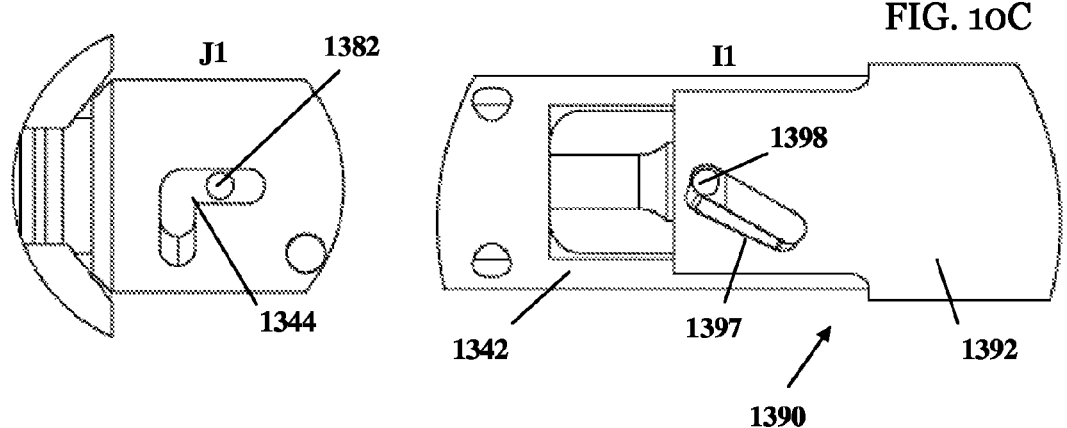
Figure 10D:
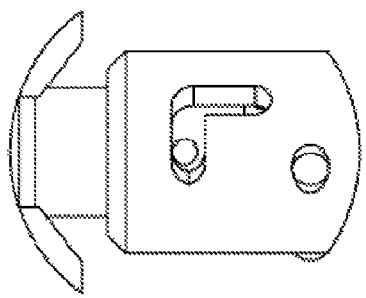
Figure 10D:
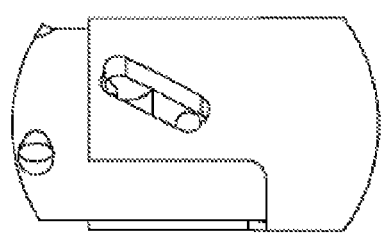
Figure 10E:
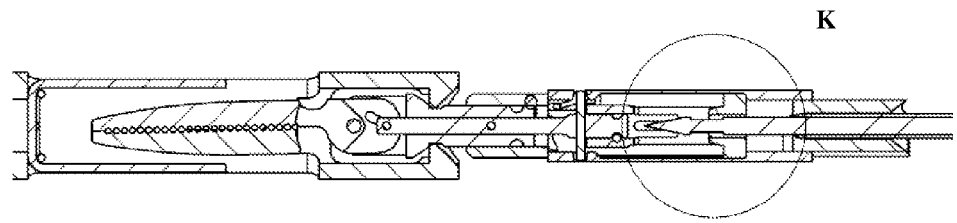

Since that pin 1398 and pin 1382 are both projections of inner shaft 1380, a counter-clockwise rotation of the inner shaft promotes a relative inward motion between tool frame 1342 and outer sleeve 1392. Referring back to FIG. 7A, releasing mechanism lock widener 1394 is situated with respect to lock beveled opening 1372 in a manner that corresponds to positions I1/J1 (FIG. 10C). In some embodiments, lock widener 1394 is firmly connected to outer sleeve 1392 in a manner that denies lengthwise movement between them, so that when frame 1342 and outer sleeve 1392 are moving inwardly, lock beveled opening 1372 and lock widener 1394 are moving inwardly as well, resulting in widening of opening 1372 by widener 1394. This allows manipulator tip 1460 removal from tool inner passage 1360, so that tool 1300 may be removed from body via port 210b. FIG. 10E illustrates the widening of opening 1372 by widener 1394 in a manner that corresponds to positions I2/J2 (FIG. 10D).

Figure 10F:
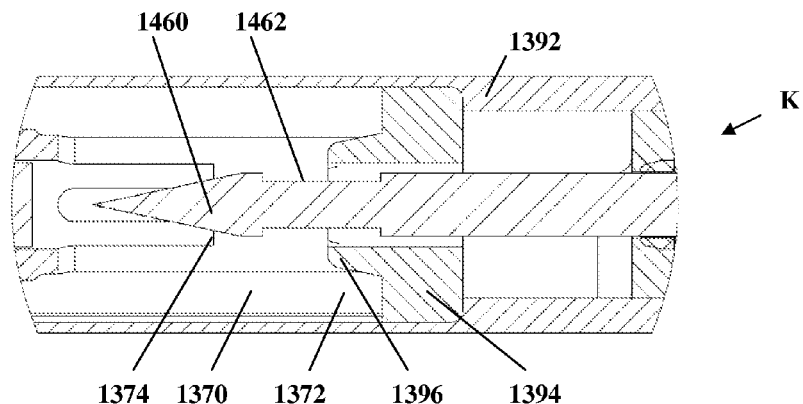
Figure 10F:
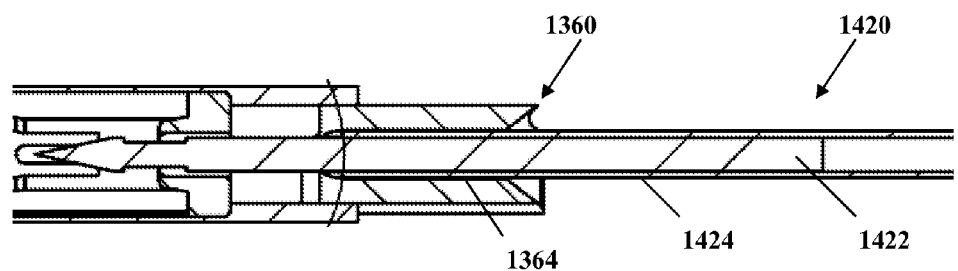

In some embodiments, the lengthwise and/or rotational movement of inner shaft 1380 (hence of pins 1398 and 1382) is executed by a corresponding motion of a manipulator body 1420. As shown in FIG. 10F, body 1420 comprises a shaft 1422 and an outer sleeve 1424, optionally capable of relative rotation. In some embodiments, tool inner passage 1360 includes at least one tenon 1364 which engages corresponding recesses or slots (not shown) on manipulator outer sleeve 1424, thereby denying rotational movement between them. Hence, in some embodiments, when manipulator 1400 is traveled inward and/or counter-clockwise rotated, tool inner shaft 1380 follows the same movement and consequently manipulator 1400 is disconnected from tool 1300 and may be easily pulled out.

(f) Other Exemplary Embodiments

In some embodiments, the system is connectible and/or is part of a surgical robotic system and/or a telesurgery system. In an exemplary embodiment, at least one of: introducer, tool, tool-cartridge, manipulator, template, template arm, are controlled and/or operated robotically and/or remotely.

In some embodiments, the system includes at least partial fail-proof locking mechanisms, for example between the tool and the tool-cartridge and/or between the tool-cartridge and the introducer and/or between the tool and the manipulator distal end. In an exemplary embodiment, a locking mechanism is normally opened, hence in a fail-mode will resume unlocked mode, or vice versa.

In some embodiments, a system locking mechanism includes pneumatic and/or hydraulic and/or electronic components. Optionally the locking mechanism includes sensors which detect connection and/or disconnections of two elements (e.g., tool and cartridge, tool and manipulator, cartridge and introducer, etc.). Optionally, in a fail-mode situation, a passive locking mechanism may be bypassed with a different active locking mechanism (e.g., remotely manually operated), and vice versa.

In some embodiments, the system is designed to allow only a specific sequence of steps. One of many sequences may include the step of connecting and/or deploying a template arm in a specific manner; followed by the step of introducing an introducer into body and pivoting cartridge to a predetermined orientation in body; followed by the step of introducing a manipulator shaft using the template arm to directly engage and connect to the tool nested or connected to the cartridge; followed by the step of releasing the tool from the cartridge. In some embodiments, this "one-way" sequence may be applied by using a control mechanism that allows a proper utilization of a second locking element only after a first locking element was properly utilized, and vice versa.

(g) Exemplary Positioning of the Tool-Introducer

System 1000 is deployed prior to utilization in a body cavity, for example, an abdominal cavity 2000. System 1000 includes a laparoscopic working channel or port, referred to here as, but not limited to, a trocar 1100, and at least one handheld micro-laparoscopic manipulator referred to as tool manipulator 1400. Tool manipulator 1400 includes a shaft 1420 and an operation handle 1440. Shaft 1420, such as a slender shaft, is configured to be attached at its distal end to a detachable and/or an interchangeable surgical end-effector or tool (not shown). In some embodiments, the tool manipulator could be configured as described herein in respect to FIG. 6-10.

Figure 11A:
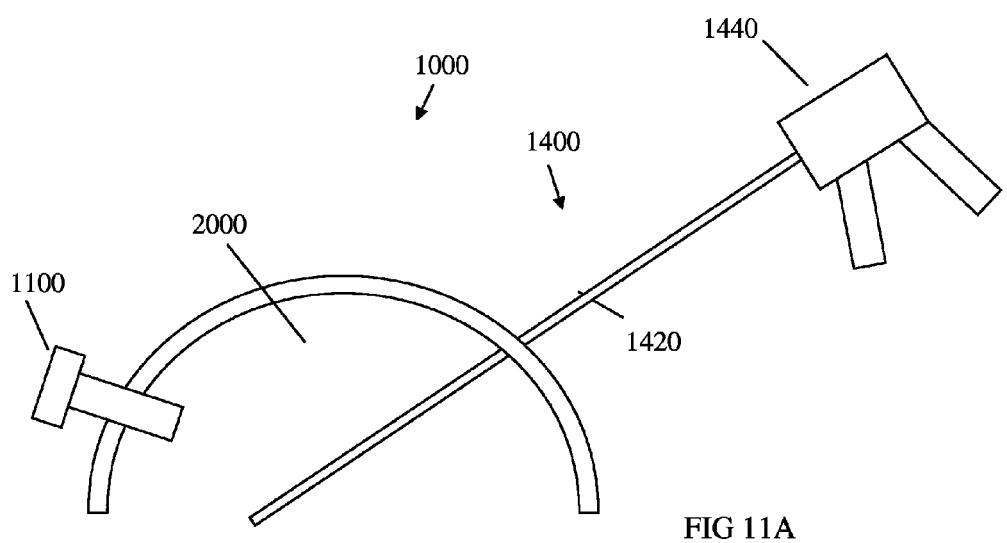
FIGS. 11A-C illustrate two alternative ways of positioning a trocar and a tool-introducer inside the body cavity for safely connecting an interchangeable tool to a manipulator, in accordance with an exemplary embodiment of the present invention.

In FIG. 11A, trocar 1100 and tool manipulator 1400 are positioned after insertion into abdominal cavity 2000 and prior to attachment of a tool. Optionally, trocar 1100 may be housing an endoscope (not shown). In order to attached the tool to the distal end of shaft 1420, the surgeon needs to position it adjacent to the lumen of trocar 1100 by aiming towards the endoscope lens (or "towards his eye" as seen in the monitor). Optionally, the endoscope is then withdrawn from trocar 1100. A tool introducer then introduces a tool through the path of the trocar 1100. In some embodiments the endoscope is deployed in the tool introducer. In some further embodiments the introduction of a tool and the transfer of the tool between a tool introducer and the shaft 1420 could be performed according to any of the methods described herein.

A tool may be any operational element (e.g., a probe or an instrument) deployable within a body, including but not limited to: surgical tools, grasping elements, dissectors, needle holders, clippers, scissors, connecting (e.g., stapling) elements, biopsy related instruments, sensor elements, imaging elements, clamping, clipping elements or grasping devices, heat generating probes (including RF, laser, IR, light, etc.), cryogenic probes, illuminating elements cutting and dissecting devices or energy sources, ultrasound probes, camera or other imaging probes, lenses, lenses tubes, or any other optical instruments, etc.

Trocar 1100 may be of any preferred size, and usually between 3 mm to 20 mm in diameter, optionally about 10 mm or 12 mm (e.g., similar in size to regular laparoscopic port). Trocar 1100 may be sized (e.g., smallest cross section) to accommodate a largest of a surgical tool in a specific tool kit. In some embodiments, system 1000 includes a single regular-sized laparoscopic port that may be utilized for tool(s) insertion into the body and/or connection to the tool manipulator 1400.

In some embodiments, shaft 1420 includes a distal tip. The largest cross section of the shaft and tip may be 0.5 mm to 5 mm in diameter, optionally 1 to 2.5 mm, optionally about 1 mm, about 1.5 mm or about 2 mm or higher or lower or intermediate. The shaft tip is optionally sharp and/or pointed in order to allow at least one of tissue penetration and easier engagement with a tool. Optionally, the shaft tip is a Veres needle which optionally permits penetration through skin and abdominal wall tissue while preventing injury of internal organs (e.g., bowels) when not "armed". Optionally, shaft 1420 includes interlocking means, e.g., threading or a groove for snap-locking (not shown), for firmly connecting with the tool, or alternatively by any means of friction, pressure or other means known to the art. Handle 1440 may be any manually operated type laparoscopic instrumentation handle or may be replaced with any robotic or other non-manually operated arm. In some embodiments, handle 1440 includes mechanisms which operate the introduced tool(s) and/or their association (e.g., locking or releasing modes or operations).

At least part of the instruments are made from rigid biocompatible materials as known to a person skilled in the art, and may include stainless steel, optionally hardened or reinforced by carbon coating or fibers, ceramic materials, plastic/polymeric materials (e.g., PEEK), composite materials (e.g., carbon-epoxy), or any combination thereof.

Figure 11B:
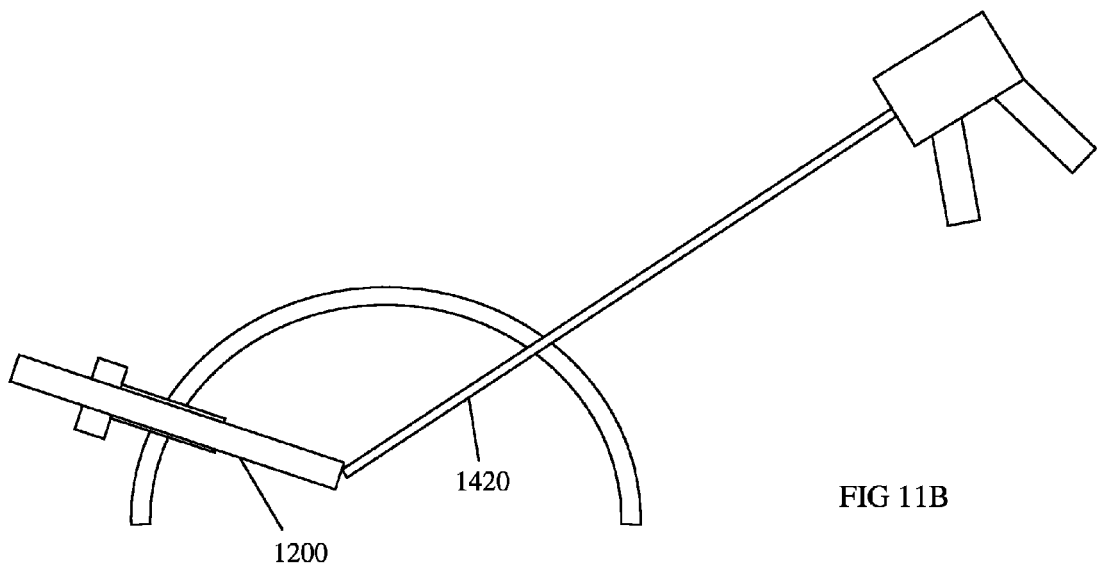
Figure 11C:
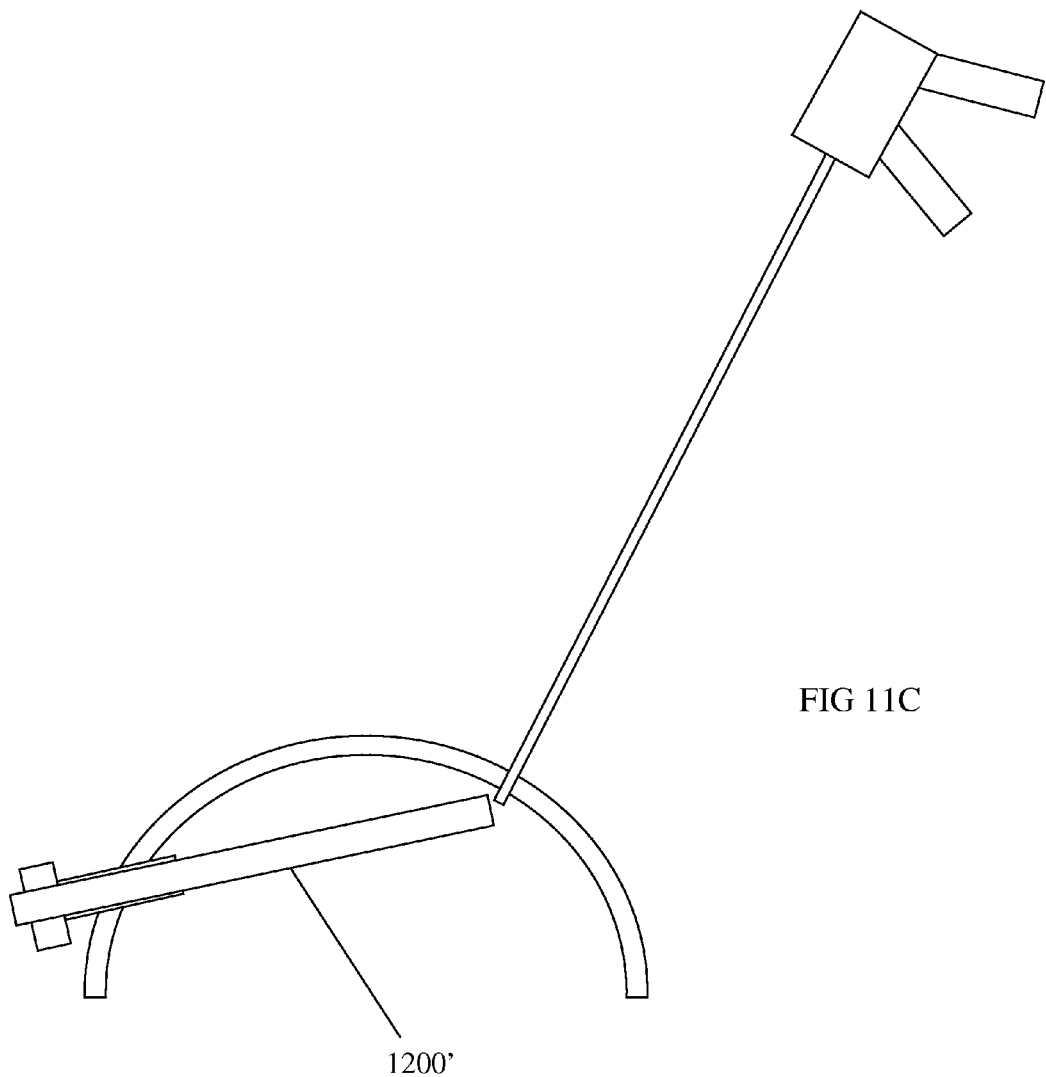

In some situations, the process of maneuvering the tool manipulator 1400 until locating the trocar 1100 may be difficult, time consuming and/or unsafe, due to the possibility that the shaft 1420 may harm adjacent tissues. Reference is now made to FIGS. 11B-C, illustrating different (partial) deployment stages of a second schematically illustrated exemplary micro-laparoscopic system, in accordance with an exemplary embodiment of the invention. This embodiment comprises an elongated tool introducer 1200 (as shown in Figs.) and/or an elongated trocar 1100 (not shown). An elongated tool introducer 1200 assists in locating and guiding distal end of shaft 1420 before transferring the tool to the shaft 1420. The elongated tool introducer 1200 is introduced via trocar 1100, and travels into the abdominal cavity 2000 until it is adjacent the distal end of shaft 1420 (as shown in FIG. 11B). In this embodiment, an endoscope (not shown) may be placed inside the elongated tool introducer 1200. Additionally and/or alternatively an elongated trocar 1100 could be used to locate and guide the distal end of shaft 1420 before introducing the tool introducer 1200 into the lumen of the trocar 1100. If an elongated trocar 1100 is utilized an endoscope could in some embodiments be placed inside the trocar 1100.

Additionally or alternatively to using an elongated trocar 1100 and/or an elongated tool introducer 1200, other locating and/or guiding and/or grasping/connecting devices (not shown) may be used to locate and/or guide and/or grasp shaft 1420 in the abdominal cavity 2000 and assist in transferring and engaging the interchangeable tool.

FIG. 11C suggests a slightly different approach using a substantially longer or more distally advanceable elongated tool introducer 1200' (shown) and/or elongated trocar 1100 (not shown), which is sized and/or configured to advance towards and to reach at and/or capture the inlet/incision or a position adjacent to the inlet/incision of manipulator 1400 through and into abdominal cavity 2000, so the tip of the shaft 1420 may be captured at the entry of the abdominal cavity 2000, located at the periphery of the abdominal cavity 2000. In some instances it will be preferable to use this approach, as may be important not only to prevent injury to organs but also to prevent working against the direction of viewing which may be considered cumbersome.

In some embodiments the release, transfer and engagement of the interchangeable tool could then be performed according to any of the methods described herein. Alternatively, such release, transfer and engagement maybe performed in other methods known to the art.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for positioning an interchangeable tool in a body cavity, the system comprising:
   a channel comprising a lumen for direct communication with said body cavity;
   a tool introducer comprising a longitudinal axis and a distal end, said tool introducer is capable of traveling through said channel lumen; and
   a tool holder covering at least a portion of said interchangeable tool, said tool holder is pivotally connected to said tool introducer distal end for angular positioning said interchangeable tool in said body cavity after said tool holder emerges from said channel,
   wherein said tool introducer comprises a tubular section.

2. The system according to claim 1, wherein said angular positioning is predetermined.

3. The system according to claim 1, wherein said angular positioning is constant.

4. The system according to claim 1, wherein said angular positioning is selectively chosen after said tool holder emerges from said channel and into said body cavity.

5. The system according to claim 1, wherein said interchangeable tool comprises one of the group consisting of a grasper, a dissector, a needle holder, scissors, a camera, an endoscope, a heat source, a sensing probe, a cryogenic probe, a dissector, a biopsy probe, a cutting tool, a laser source, an IR source, a light source, an illumination source, an ultrasound probe, an electrocautery device, a drug delivery device and combinations thereof.

6. The system according to claim 1, and further comprising an endoscope deployable in said tubular section.

7. The system according to claim 6, wherein said tubular section includes a window, thereby enabling endoscopic visualization by said endoscope.

8. A system for positioning an interchangeable tool in a body cavity, the system comprising:
   a channel comprising a lumen for direct communication with said body cavity;
   a tool introducer comprising a longitudinal axis and a distal end, said tool introducer is capable of traveling through said channel lumen;
   a tool holder covering at least a portion of said interchangeable tool, said tool holder is pivotally connected to said tool introducer distal end for angular positioning said interchangeable tool in said body cavity after said tool holder emerges from said channel; and
   an external guiding device configured to guide a tool manipulator to engage said interchangeable tool in said body cavity, said guiding device comprising a center guide comprising a first lumen adapted to accommodate said channel and an adjustable peripheral guide having a proximal end connected to said center guide and a distal end incorporating a second lumen;
   wherein said tool introducer is distally connected to said interchangeable tool and readily deployable in said body cavity through said channel accommodated in said first lumen of said center guide, and
   wherein said adjustable peripheral guide is adjusted to guide said tool manipulator through said second lumen to engage said interchangeable tool.

9. The system according to claim 8, wherein said external guiding device is further adapted to guide a distal portion of said tool manipulator in a defined orientation and/or depth in said body cavity.

10. The system according to claim 9, wherein said external guiding device is adapted to selectively lock said distal portion of said tool manipulator in said orientation and/or depth.

11. The system according to claim 9, wherein said distal portion of said tool manipulator is concentric to an inner passage of said interchangeable tool.

12. The system according to claim 8, wherein said second lumen includes a longitudinal axis that is angled towards said center guide in at least one dimension.

13. The system according to claim 8, wherein said adjustable peripheral guide is adjustable by at least one of: lengthening, bending, tilting, rotating, deforming and/or any combination thereof.

14. A method for engaging an interchangeable tool, said interchangeable tool having an inner passage, with a distal portion of a tool manipulator in a body cavity, said method comprising the steps of:
   inserting a tool introducer into a channel, said channel comprising a lumen providing direct communication into said body cavity and wherein a proximal end of said interchangeable tool is reversibly connected to a distal end of said tool introducer;
   orienting said distal portion of said tool manipulator in said body cavity;
      emerging said interchangeable tool from said channel into said body cavity; and positioning said interchangeable tool eccentrically to said lumen of said channel
   wherein said inner passage of the interchangeable tool is angled towards said distal portion of said tool manipulator.

15. The method according to claim 14, wherein said positioning is automatically executed once said interchangeable tool entirely emerges from said channel.

16. The method according to claim 14, wherein said positioning is selectively executed by an operator.

17. The method according to claim 14, and further comprising predetermining an angle of said positioning of said interchangeable tool.

18. The method according to claim 14, comprising using a constant angle for said positioning of said interchangeable tool.

19. The method according to claim 14, and further comprising selectively choosing an angle of said positioning of said interchangeable tool after emerging said interchangeable tool.

* * * * *